US010022721B2

(12) United States Patent
Kiani et al.

(10) Patent No.: US 10,022,721 B2
(45) Date of Patent: Jul. 17, 2018

(54) MICROFLUIDIC DEVICES AND METHODS OF THEIR USE

(71) Applicant: Bio-Rad Laboratories, Inc., Hercules, CA (US)

(72) Inventors: Sepehr Kiani, Watertown, MA (US); Joshua Blouwolff, Brookline, MA (US); Adnan Esmail, Boston, MA (US); Jason Hung, Arlington, MA (US); Tony Hung, Cambridge, MA (US); Adam R. Abate, San Francisco, CA (US); Scott Powers, Cambridge, MA (US); Pascaline Mary, Cambridge, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 905 days.

(21) Appl. No.: 14/470,860

(22) Filed: Aug. 27, 2014

(65) Prior Publication Data
US 2015/0065396 A1 Mar. 5, 2015

Related U.S. Application Data

(60) Provisional application No. 61/870,336, filed on Aug. 27, 2013, provisional application No. 61/875,312, (Continued)

(51) Int. Cl.
*B01L 3/00* (2006.01)
*C12N 15/10* (2006.01)
(Continued)

(52) U.S. Cl.
CPC ..... *B01L 3/502784* (2013.01); *B01L 3/50273* (2013.01); *B01L 3/502738* (2013.01);
(Continued)

(58) Field of Classification Search
CPC ..... B01L 2300/0867; B01L 2400/0487; B01L 3/502784; B01L 2200/0621;
(Continued)

(56) References Cited

U.S. PATENT DOCUMENTS 8,528,589 B2  9/2013  Miller et al.
8,535,889 B2  9/2013  Larson et al.
(Continued)

FOREIGN PATENT DOCUMENTS

CN  102483424 A  5/2012
EP  2364774 A2  9/2011
(Continued)

OTHER PUBLICATIONS

Cristobal et al. "Microfluid bypass for efficient passive regulation of droplet traffic at a junction", Applied Physics Letters. 89: 034104, 2006.*
(Continued)

*Primary Examiner* — Jennifer Wecker
(74) *Attorney, Agent, or Firm* — Kilpatrick Townsend and Stockton LLP

(57) ABSTRACT

Methods and systems for manipulating drops in microfluidic channels are provided.

12 Claims, 19 Drawing Sheets

Related U.S. Application Data filed on Sep. 9, 2013, provisional application No. 61/881,040, filed on Sep. 23, 2013, provisional application No. 61/905,914, filed on Nov. 19, 2013, provisional application No. 61/905,927, filed on Nov. 19, 2013, provisional application No. 61/934,889, filed on Feb. 3, 2014, provisional application No. 61/896,766, filed on Oct. 29, 2013.

(51) Int. Cl.
*C12Q 1/68* (2018.01)
*G01N 27/00* (2006.01)
*B01L 7/00* (2006.01)
*C12M 1/00* (2006.01)

(52) U.S. Cl.
CPC .......... *C12N 15/1075* (2013.01); *B01L 7/525* (2013.01); *B01L 2200/025* (2013.01); *B01L 2200/0621* (2013.01); *B01L 2200/0684* (2013.01); *B01L 2200/10* (2013.01); *B01L 2200/16* (2013.01); *B01L 2300/021* (2013.01); *B01L 2300/0645* (2013.01); *B01L 2300/0654* (2013.01); *B01L 2300/0672* (2013.01); *B01L 2300/087* (2013.01); *B01L 2300/0864* (2013.01); *B01L 2300/0867* (2013.01); *B01L 2300/0887* (2013.01); *B01L 2400/0487* (2013.01); *B01L 2400/0655* (2013.01); *B01L 2400/0683* (2013.01); *B01L 2400/0688* (2013.01); *B01L 2400/084* (2013.01)

(58) Field of Classification Search
CPC ............. B01L 2200/10; B01L 2200/16; B01L 2300/0672; B01L 2300/087; B01L 2300/0887; B01L 2400/0638; B01L 2400/0655; B01L 2400/0683; B01L 3/50273; B01L 3/502738; B01L 2200/0684; B01L 2400/0688; B01L 2200/025; B01L 2300/021; B01L 2300/0645; B01L 2300/0654; B01L 2300/0864; B01L 2400/084; B01L 7/525; F16K 99/00; F16K 99/0015; F16K 99/0059; C12N 15/1075

See application file for complete search history.

(56) References Cited

U.S. PATENT DOCUMENTS

| | | | |
|---|---|---|---|
| 2005/0087122 A1* | 4/2005 | Ismagliov | B01F 5/0646 117/2 |
| 2007/0141593 A1* | 6/2007 | Lee | G01N 27/44769 435/6.11 |
| 2008/0014589 A1* | 1/2008 | Link | B01F 3/0807 435/287.2 |
| 2010/0285975 A1 | 11/2010 | Mathies et al. | |
| 2011/0000560 A1 | 1/2011 | Miller et al. | |
| 2011/0151578 A1 | 6/2011 | Abate et al. | |
| 2011/0218123 A1 | 9/2011 | Weitz et al. | |
| 2011/0250597 A1 | 10/2011 | Larson et al. | |
| 2011/0267457 A1 | 11/2011 | Weitz et al. | |
| 2012/0015822 A1 | 1/2012 | Weitz et al. | |
| 2012/0091004 A1 | 4/2012 | Abell et al. | |
| 2012/0132288 A1* | 5/2012 | Weitz | B01F 5/0471 137/13 |
| 2012/0219947 A1 | 8/2012 | Yurkovetsky et al. | |
| 2012/0220494 A1 | 8/2012 | Samuels et al. | |
| 2012/0222748 A1 | 9/2012 | Weitz et al. | |
| 2012/0309002 A1 | 12/2012 | Link | |
| 2014/0354795 A1 | 12/2014 | Tracy et al. | |
| 2015/0024945 A1 | 1/2015 | Healy | |

FOREIGN PATENT DOCUMENTS

| | | |
|---|---|---|
| EP | 2662135 A2 | 11/2013 |
| WO | 2007/081385 A2 | 7/2007 |
| WO | 2007/081387 A1 | 7/2007 |
| WO | 2012/078710 A1 | 6/2012 |
| WO | 2012/135201 A1 | 10/2012 |
| WO | 2012/135259 A1 | 10/2012 |
| WO | 2012/135327 A1 | 10/2012 |
| WO | 2013/095737 A2 | 6/2013 |
| WO | 2013/122826 A1 | 8/2013 |
| WO | 2013/165748 A1 | 11/2013 |
| WO | 2014/043388 A1 | 3/2014 |
| WO | 2014/093976 A1 | 6/2014 |
| WO | 2014/117088 A1 | 7/2014 |
| WO | 2014/176599 A1 | 10/2014 |

OTHER PUBLICATIONS

The International Search Report and Written Opinion from PCT/US2014/052995, dated Jan. 21, 2015.

Cristobal et al. Microfluid bypass for efficient passive regulation of droplet traffic at a junction. *Applied Physics Letters.* 89:034104. 2006. [retrieved on Jan. 7, 2015]. Retrieved from the Internet. <URL: http://lof.cnrs.fr/IMG/pdf/Microfluidic_bypass_for_efficient_passive_regulation_of_dropplet_traffi c_at_ajunction.pdf>.

Zheng et al. Formation of Droplets of Alternating Composition in Microfluidic Channels and Applicantions to Indexing of Concentrations in Droplet-Based Assays. *Analytical Chemistry.* 6(17):4977-4982. 2004. [retrieved on Jan. 6, 2015]. Retrieved from the Internet. <URL: http://www.ncbi.nlm.nih.gov/pmc/articles/PMC1766978/>.

U.S. Appl. No. 14/502,948, filed Sep. 30, 2014.

Extended European Search Report from EP Application 14840221.7; dated Mar. 2, 2017; 9 pages.

English translation of First Office Action from Chinese Patent Application 201480047519.3; dated Mar. 8, 2017; 14 pages.

* cited by examiner

Microfluidic Device 6140

MICROFLUIDIC DEVICES AND METHODS OF THEIR USE

CROSS-REFERENCES TO RELATED APPLICATIONS

The present application claims benefit of priority to each of the following US Provisional Patent Applications, each of which are incorporated by reference in their entirety: 61/870,336, filed Aug. 27, 2013; 61/875,312, filed Sep. 9, 2013; 61/896,766, filed Oct. 29, 2013; 61/905,914, filed Nov. 19, 2013; 61/881,040, filed Sep. 23, 2013; 61/905,927, filed Nov. 19, 2013; and 61/934,889, filed Feb. 3, 2014.

BACKGROUND OF THE INVENTION

Microfluidic processes often employ the use of an emulsion, which contains drops of a dispersed liquid phase surrounded by an immiscible continuous liquid phase. Drops may be used as reaction vessels for chemical or biological reactions, as storage vessels, and/or as a method to isolate and compartmentalize molecules, such as chemical or biological elements. With proper chemistry such as surfactants on the surface of the emulsion, drops may be made "stable," meaning they are substantially prevented form mixing and merging when in contact with each other. This stability allows one to create a population or library of drops composed of different chemical or biological components that may be stored in the approximately same volume of space without mixing or contamination between and/or among the components of one drop and another.

Currently, drops flow within a microfluidic device where many drops are injected with sample from a single large drop (herein referred to interchangeably as either a "large drop" or "slug") or one more discrete inline samples. Often times "sets" of drops are created, meaning that a sequential number of drops will be injected with the same type of larger drop, resulting in a set of substantially similar drops. It is possible to have many sets of drops within a given sample. As the newly injected drops flow throughout the microfluidic channels within the microfluidic device, the drops often mix and rearrange themselves, resulting in the loss of defined sets of drops, causing issues downstream in detection and data analysis.

In some cases, it can be advantageous to label emulsion drops in a microfluidic network with a sample of interest in an alternating fashion. Doing so ensures that they are distinguishable when the drops proceed to a subsequent detection process, without detection overlap between adjacent drops. For example, sets of drops as discussed above can be distinguished by having different labels or by one set having a label and the other set lacking the label.

Microfluidic devices can use liquid emulsions comprised of a continuous phase and a dispersed phase, wherein the dispersed phase may include droplets that serve as vessels within which chemical or biological reactions may be performed. To perform these reactions, different functions can be performed on the droplets, such as the loading of reagents and reaction components (e.g., cells, proteins and nucleic acids) into the droplets, followed by incubating, sorting and/or optically detecting the droplets. For example, when introducing multiple reagents into one or more droplets, the volume of the continuous phase between droplets can be such that reagents are injected into any given droplet sequentially, i.e., one at a time rather than more than one at a time to avoid cross-contamination. Conversely, when storing the droplets in an incubation chamber or passing the droplets through an incubation channel, the volume fraction of the continuous phase must be reduced such that the droplets are packed closely and move in unison at a constant velocity, as well as to minimize the amount of space required within the microfluidic device.

These and other issues are addressed herein.

BRIEF SUMMARY OF THE INVENTION

In some embodiments, a system for alternating flow of two or more previously formed, differentially labeled population of droplets is provided. in some embodiments, the system comprises: a microfluidic device with two or more inlets for differentially-labeled droplets, and at least two microfluidic channels that form a junction with a joint microfluidic channel, wherein the system is configured to allow the droplets to flow from the two or more inlets through the microfluidic channels toward the joint microfluidic channel in an alternating fashion.

In some embodiments, the system further comprises a connection channel, in fluid communication with and between the two microfluidic channels, said connection channel configured to allow a continuous phase fluid but not the droplets to flow between the microfluidic channels.

Also provided are methods of alternating flow of two or more previously formed differentially labeled population of droplets. In some embodiments, the method comprising, providing the microfluidic device of claim 1 or 2, wherein first droplets in a first inlet of the two or more inlets and second droplets in a second inlet of the two or more inlets are differentially labeled; and causing the first and second droplets to flow into the joint microfluidic channel in an alternating fashion.

Also provided is a system for labeling and alternating flow of differentially-labeled droplets. In some embodiments, the system comprises: at least one inlet for droplets within a continuous phase, at least two microfluidic channels that are connected to the at least one inlet at one end and form a junction with a joint microfluidic channel at the other end, and a labeling device configured to label droplets in one of the microfluidic channels; wherein when the droplets flow through the at least two microfluidic channels toward the joint microfluidic channel, the labeling device labels the droplets that flow in one of the microfluidic channels.

In some embodiments, said label is an immiscible label.

In some embodiments, the labeling device labels the droplets through disrupting the interface between the immiscible label and the continuous phase. In some embodiments, the labeling device uses an electric field to disrupt the interface between the immiscible label and the continuous phase. In some embodiments, the labeling device comprises one or more electrodes that generate an electric field to disrupt the interface between the immiscible label and the continuous phase. In some embodiments, the droplets in the microfluidic channel is spaced so that neighboring droplets do not coalesce due to the presence of the electric field. In some embodiments, the system further comprises a connection channel that allows the continuous phase fluid but not the droplets to flow between the microfluidic channels.

Also provided is a method for labeling droplets and alternating flow of differentially-labeled droplets. In some embodiments, the method comprises: injecting a plurality of droplets within a continuous phase into at least one inlet that connects to at least two microfluidic channels, wherein the microfluidic channels are connected to the at least one inlet at one end and form a junction with a joint microfluidic channel at the other end, and labeling the droplets in one of the microfluidic channels with a label with a labeling device, wherein labeled and unlabeled droplets enter the joint microfluidic channel in a substantially alternating fashion.

In some embodiments, said label is an immiscible label.

In some embodiments, the droplets contain primers and reagents that are necessary for a desired PCR reaction. In some embodiments, the system further comprises a connection channel that allows a continuous phase fluid but not the droplets to flow between the microfluidic channels. In some embodiments, the labeling device labels the droplets through disrupting the interface between the immiscible label and the continuous phase. In some embodiments, the labeling device comprises one or more electrodes that generate an electric field to disrupt the interface between the immiscible label and the continuous phase. In some embodiments, the droplets in the microfluidic channel are spaced so that neighboring droplets do not coalesce due to the presence of the electric field.

Also provided is a method of dividing a plurality of drops comprising at least a first and second set of drops within an emulsion in a microfluidic channel. In some embodiments, the method comprises generating a spacer drop at a location between a first and second set of drops in an emulsion in the microfluidic channel, wherein the drops of the first and second set are of substantially the same volume and the spacer drop has a larger volume than the average volume of the drops of the first or second set, thereby dividing the plurality of drops in the microfluidic channel.

In some embodiments, a plurality of sets of drops are introduced into the microfluidic channel and a plurality of spacer drops is introduced into the microfluidic channel such that a spacer drop separates different sets of drops. In some embodiments, the emulsion comprises the drops contained in an immiscible fluid, and following introduction of the spacer drop, the amount of immiscible fluid in the continuous phase of the emulsion is reduced, thereby compacting the plurality of drops into a smaller space compared to immediately prior to the introducing. In some embodiments, the generating comprises introducing the spacer drop from a side channel at said location in a microfluidic channel. In some embodiments, the spacer drop does not contain proteins or nucleic acids.

In some embodiments, the generating comprises merging two or more drops from one or more adjacent sets to generate a spacer drop between two sets, In some embodiments, the method further comprises optically monitoring the sets of drops in the microfluidic channel upstream of the side channel, and triggering the generating of the spacer drop(s) based on results of the optically monitoring, thereby introducing spacer drops based on the identity of the sets of drops.

In some embodiments, the generating occurs at a fixed rate.

In some embodiments, upstream in the microfluidic channel from said location, portions of drops from an upstream side channel are injected into drops from further upstream in the microfluidic channel such that sets of drops are defined as all drops containing a portion of the same drop from the upstream side channel. In some embodiments, the drops in said upstream side channel comprise amplified DNA. In some embodiments, different drops in said upstream side channel comprise different amplicons. In some embodiments, said drops from further upstream in the microfluidic channel comprise one or more polynucleotide hybridization probes.

Also provided is a device comprising a microfluidic channel, the microfluidic channel comprising at least a first and second set of drops within an emulsion, wherein the drops of the first and second set are of substantially the same volume and the first and second sets are divided by a spacer drop having a larger volume than the average volume of the drops of the first or second set. In some embodiments, the spacer drop does not contain proteins or nucleic acids.

Also provided is a system for performing a controlled change in the continuous phase volume fraction from an emulsion, wherein the system comprises a microfluidic device comprising one or more microfluidic channels and one or more relatively smaller channels or membranes in fluid communication with at least one of the microfluidic channels. In some embodiments, the one or more microfluidic channels are in the form of a concentric tube comprising small holes or membrane surface along the inner aspect of the tube. In some embodiments, the one or more extraction channels or membranes are arranged at an angle other than substantially perpendicular to one or more microfluidic channels. In some embodiments, the system further comprises two or more microfluidic channels arranged at an angle or position other than substantially parallel to each other.

In some embodiments, the microfluidic device comprises a first microfluidic channel and a second microfluidic channel, wherein the second microfluidic channel is controllably pressurized such that when an emulsion is introduced into the microfluidic device, a controlled volume fraction of continuous phase of the emulsion flows out of the first microfluidic channel, through the one or more extraction channels or membranes and into the second microfluidic channel, and wherein dispersed phase of the emulsion remains in the first microfluidic channel.

In some embodiments, the dispersed phase comprises a plurality of aqueous droplets. In some embodiments, the droplets each comprise a size range of from about 0.5 to about 5000 microns in diameter. In some embodiments, the continuous phase comprises an immiscible oil. In some embodiments, the immiscible oil is selected from fluorocarbon oil, silicon oil and hydrocarbon oil. In some embodiments, the hydrocarbon oil is selected from petroleum and mineral oil.

Also provided is a method for performing a controlled change in the continuous phase volume fraction from an emulsion using the system as described above or elsewhere herein, wherein the emulsion comprises an immiscible fluid continuous phase comprising aqueous drops. In some embodiments, the method comprises introducing an emulsion comprising drops into the microfluidic channel and exposing the microfluidic channel to a first pressure; and moving the emulsion past the fluid communication with the relatively smaller channel(s), wherein the relatively smaller channels are exposed to a second pressure and wherein the second pressure is lower than the first pressure such that the immiscible fluid continuous phase in the emulsion moves from the microfluidic channel to the relatively smaller channels, thereby concentrating drop concentration in the remaining emulsion in the microfluidic channel.

In some embodiments, the method comprises introducing an emulsion comprising drops into the microfluidic channel and exposing the microfluidic channel to a first pressure; and moving the emulsion past the fluid communication with the relatively smaller channel(s), wherein the relatively smaller channels comprise an immiscible fluid continuous phase and are exposed to a second pressure and wherein the second pressure is higher than the first pressure such that the immiscible fluid continuous phase relatively smaller channel(s) moves from the relatively smaller channels to the microfluidic channel, thereby reducing the drop concentration in the emulsion in the microfluidic channel.

Also provided is a device comprising at least one microfluidic channel, the channel comprising a first narrow portion of the channel and a second wider portion of the channel, wherein the second wider portion comprises a series of posts within the wider portion and one or more outlets for removal of an immiscible fluid continuous phase from an emulsion in the microfluidic channel, wherein the series of posts are arranged to substantially maintain the order of drops within the emulsion along the microfluidic channel. In some embodiments, the second wider portion comprises one or more side channels in fluid communication with the second wider portion. In some embodiments, the side channels are less wide than the width of the second wider portion.

Also provided is a method of removing immiscible fluid continuous phase from an emulsion comprising aqueous drops. In some embodiments, the method comprises introducing the emulsion into the microfluidic channel such that the emulsion moves from the first portion with drops in a certain order to the second wider portion, wherein when the emulsion enters the second portion, some immiscible fluid continuous phase from the emulsion is removed from the second wider portion while the drops substantially maintain the order of the drops from the first portion of the channel. In some embodiments, the second wider portion comprises one or more side channels in fluid communication with the second wider portion and the immiscible fluid continuous phase is removed via the side channels.

Also provided is a device comprising: an emulsion microfluidic channel and a continuous phase microfluidic channel joined to the emulsion microfluidic channel at a junction in the emulsion microfluidic channel, wherein the emulsion microfluidic channel comprises a channel portion (i) having a width that is no larger than 0.8, 0.9, 1.0, 1.2, 1.5, 2, 3, 4, 5, 6 times the diameter of drops in the emulsion and (ii) that gradually widens immediately before the junction and (iii) gradually narrows immediately after the junction to a width that is no larger than 0.8, 0.9, 1.0, 1.2, 1.5, 2, 3, 4, 5, 6 times the diameter of drops.

In some embodiments, the continuous phase microfluidic channel is in fluid communication with a continuous phase reservoir. In some embodiments, the emulsion microfluidic channel comprises an emulsion and the continuous phase microfluidic channel comprises a continuous phase immiscible fluid. In some embodiments, the channel portion is substantially the same as the diameter of drops.

Also provided is a method of introducing an immiscible continuous fluid into an emulsion to space drops within the emulsion. In some embodiments, the method comprises: introducing the emulsion into a device as described above or elsewhere herein such that drops in the emulsion occur in single file in the emulsion microfluidic channel; introducing additional immiscible continuous phase fluid into the emulsion from the continuous phase microfluidic channel such that drops flowing past the junction of the emulsion microfluidic channel and the continuous phase microfluidic channel are spaced farther apart from each other than drops in the emulsion upstream of the junction.

Also provided is a device comprising, a chamber for holding an emulsion comprising drops; connected to the chamber, two or more parallel microfluidic chambers having a width substantially the same as the diameters of the drops. In some embodiments, an optical detector is configured to detect drops in one or more of the parallel microfluidic chambers.

In some embodiments, the two or more parallel microfluidic channels merge into a single channel or chamber. In some embodiments, the two or more parallel microfluidic channels are in fluid communication with one or more reservoirs for delivering additional immiscible fluid continuous phase to further space drops within the emulsion in the parallel microfluidic channels.

Also provided is a method of distributing drops evenly into two or more parallel microfluidic channels. In some embodiments, the method comprises providing an emulsion in the chamber of a device as described above or elsewhere herein, wherein the emulsion comprises drops in an immiscible fluid continuous phase, and providing a pressure on the emulsion in the chamber to push the emulsion into the two or more parallel microfluidic channels, thereby distributing the drops from the chamber evenly into the two or more parallel microfluidic channels.

In some embodiments, the method further comprises detecting one or more characteristic of the drops while the drops are within the microfluidic channels.

In some embodiments, the method further comprises merging the emulsions in the two or more parallel microfluidic channels into a second chamber or channel.

Also provided is a device comprising a series of microfluidic channels, wherein the series of channels comprises at least one channel that divides at a junction into two downstream microfluidic channels, wherein one or more shunt channels connecting the two downstream microfluidic channels. In some embodiments, each of the two downstream microfluidic channels further divide into two further downstream microfluidic channels, wherein one or more shunt channels connect the two further downstream microfluidic channels. In some embodiments, the microfluidic channels comprise an emulsion comprising drops and downstream microfluidic channels merge to form one or more consolidated channels.

Also provided is a method of distributing drops evenly into two or more microfluidic channels. In some embodiments, the method comprises introducing an emulsion comprising drops into the channel of the device as described above or elsewhere herein, and applying a pressure such that the emulsion enters the two downstream microfluidic channels, wherein the shunt channels equalize pressure between the two microfluidic channels, thereby resulting in equal distribution of drops from the emulsion between the two microfluidic channels.

DEFINITIONS

A "sample(s)", "one or more samples", or "sample(s) of interest" are terms used interchangeably in singular or plural form and are not intended to be limited to any particular quantity and, as used herein, may be any molecule or substance that the user wishes to gather information from. A sample may become larger or smaller (e.g., by way of inflation or partitioning, respectively) in size, volume or content during the performance of an assay. Accordingly, a sample may be amplified and/or subdivided one or more times during the performance of an assay. In some embodiments, the sample comprises nucleic acids.

A "fluid", as used herein, is any aqueous or lipophilic phase capable of flowing freely. Two or more fluids may flow in a manner referred to as "co-flowed" such that the flow of each fluid is laminar in the same direction within the range or timescale of the operation of the system but such that they are not substantially mixing. The fluid and/or emulsion injected into or out of a droplet may further comprise one or more reagents, reaction components or samples of interest selected from cells (including any eukaryotic or prokaryotic cells, including but not limited to cells selected from humans, animals, plants, fungi, bacteria, viruses, protozoa, yeasts, molds, algae, rickettsia, and prions); proteins, peptides, nucleic acid sequences, oligonucleotide probes, polymerase enzymes, buffers, dNTPs, organic and inorganic chemicals, and fluorescent dyes.

An "emulsion", as used herein, is a stable mixture of at least two immiscible or partially immiscible liquids. In general, immiscible liquids tend to separate into two distinct phases. Accordingly, a surfactant may be added to stabilize the emulsion by reducing surface tension between the at least two immiscible or partially immiscible liquids and/or to stabilize the interface. For example, an emulsion according to the systems, methods and kits of this invention may comprise a plurality of aqueous drops in an immiscible oil, such as fluorocarbon oil, silicon oil or hydrocarbon oil (including, but not limited to, petroleum and mineral oil) where the drop size ranges from about 0.5 to about 5000 microns in diameter.

Figure 10:
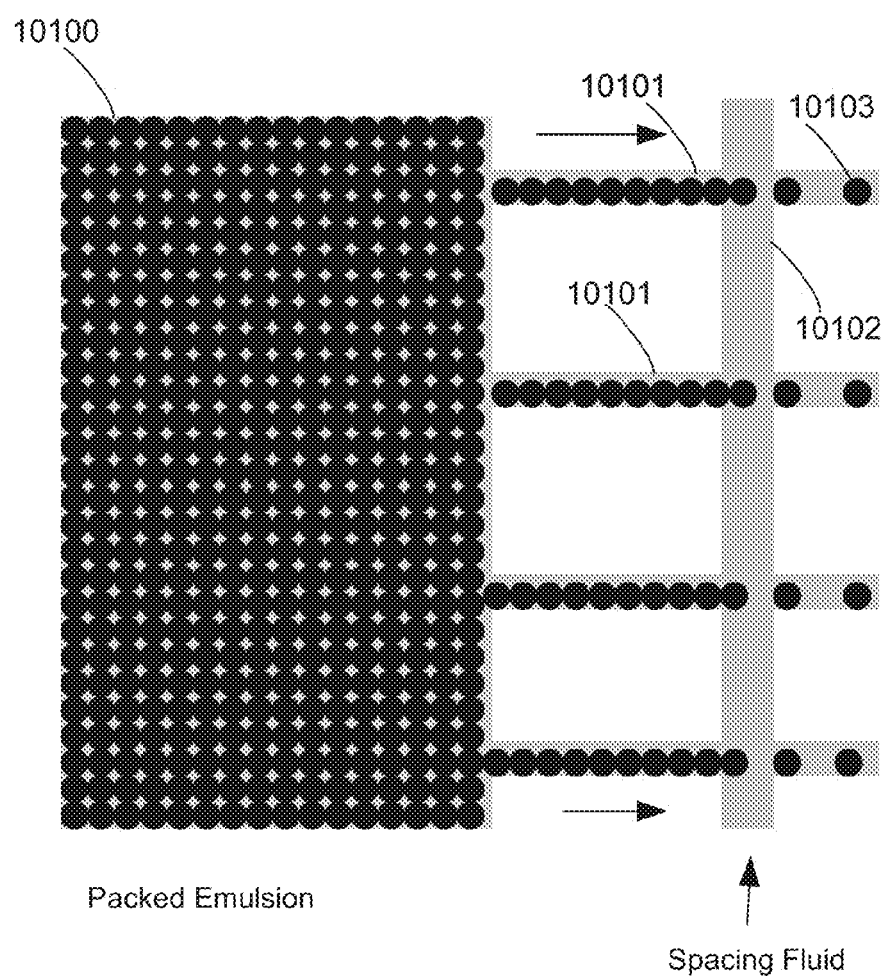

The droplet distributor in FIG. 10 shows a device in which the feed channel is much larger than the exit channels. Consequently, a majority of the pressure decrease through the device originates from the exit channels, the pressure in the feed channel is essentially constant, and the drops are distributed evenly though the exit channels.

Figure 11:
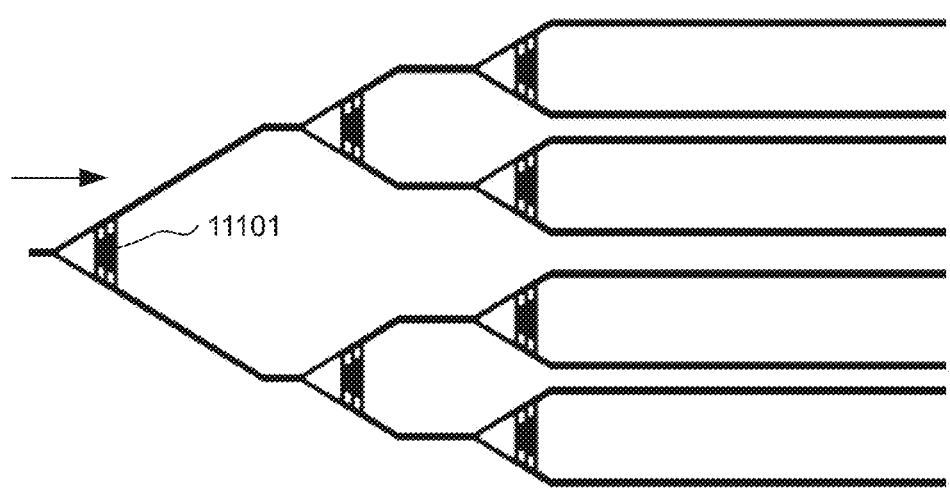

The distributor in FIG. 11 uses a different method to evenly distribute the drops, in which shunted bifurcations allow pressure fluctuations to feedback, and cause the drops to flow in an alternating pattern through the channels.

Figure 12:
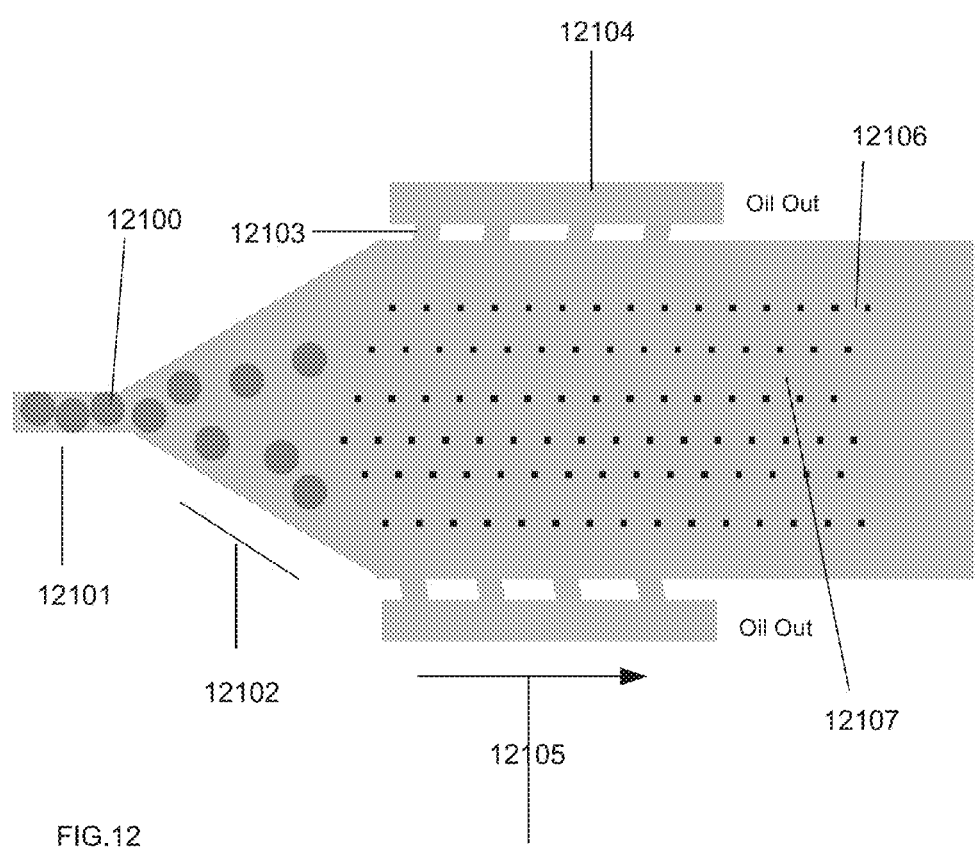

FIG. 12 illustrates a channel within a microfluidic device. The channel gradually widens and introduces oil-removing sister channels in addition to the incorporation of small posts within the channel, providing for easy oil separation and allowing the approaching drops to maintain their order within the channel.

Figure 13:
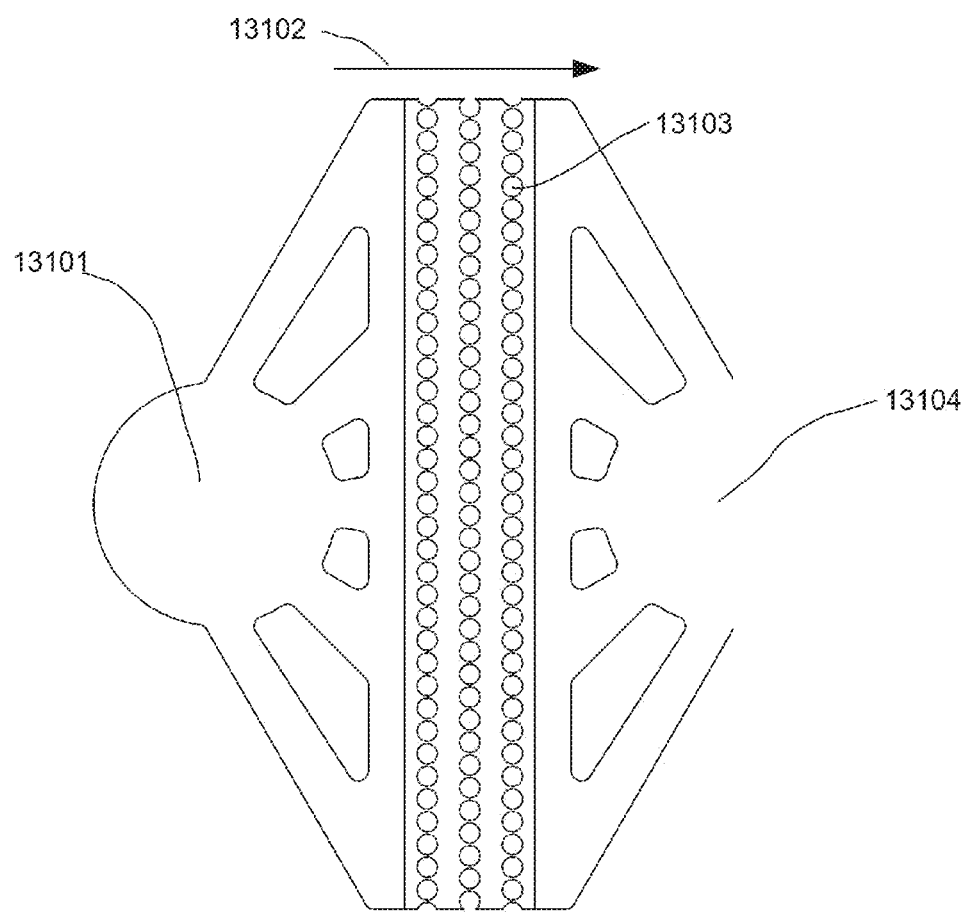

FIG. 13 depicts one embodiment of the overall droplet filter architecture from one view, e.g., 40 µm drops.

Figure 14A:
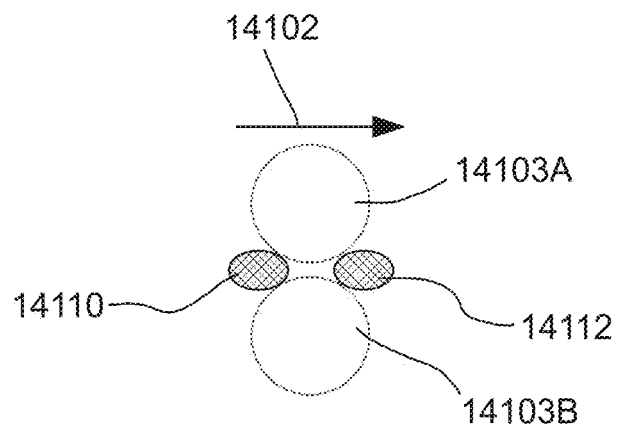
Figure 14B:
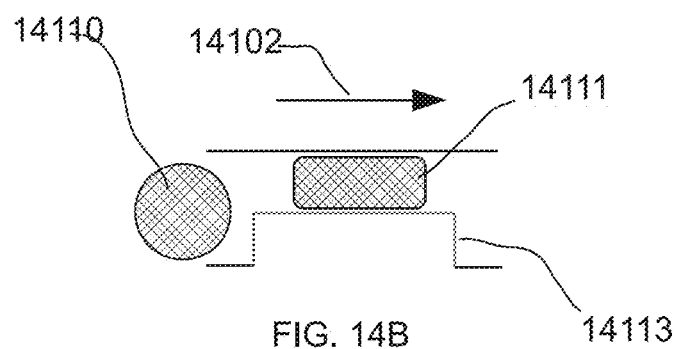
Figure 14C:
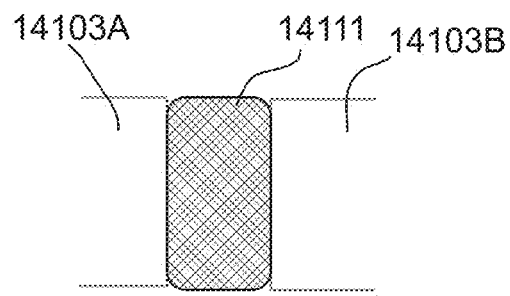

FIGS. 14A, 14B, and 14C show different sectional views in order to illustrate droplet flow, viewed from three different vantage points. FIG. 14A illustrates one embodiment view from a topographical orientation. FIG. 14B illustrates one embodiment view from a side view. FIG. 14C illustrates one embodiment view from a front view.

Figure 15:
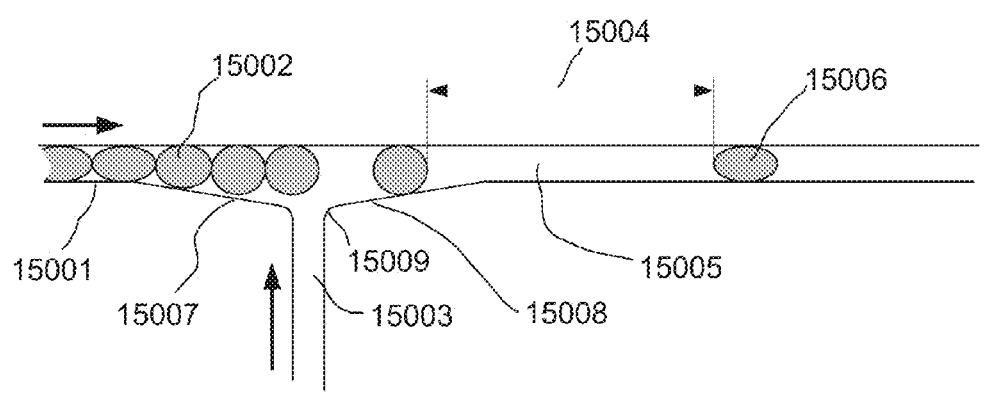

FIG. 15 describes one embodiment of a high speed droplet spacer.

Figure 16:
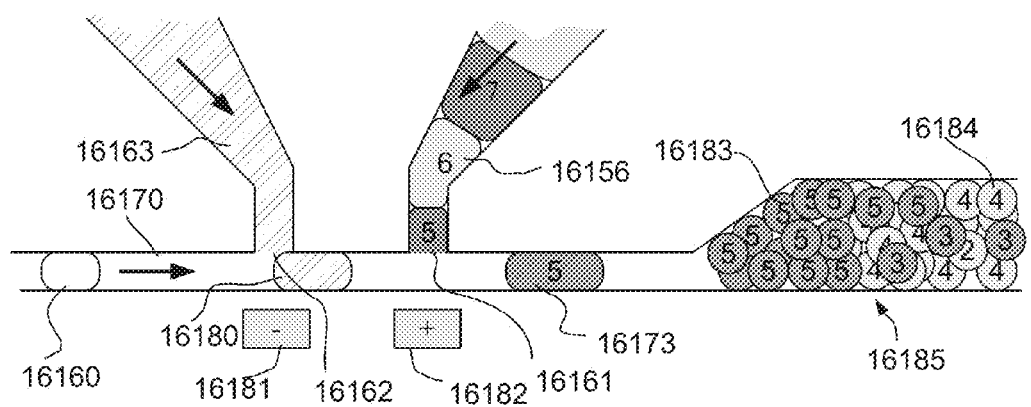

FIG. 16 is an illustration of an example of one embodiment of a system and method where sets of drops downstream from injection sites are mixed within the channel, creating a problem in detection and data analysis.

Figure 17:
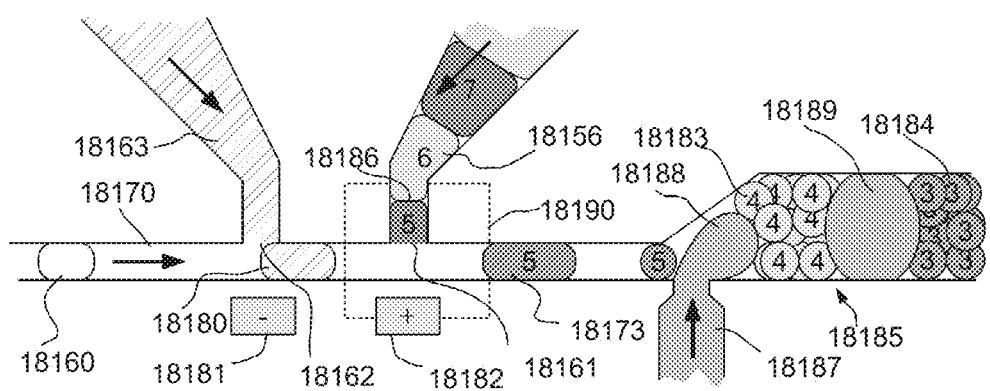

FIG. 17 is an illustration of an example of one embodiment of a system and method where sets of drops downstream from injection sites are prevented from mixing within the channel by a synchronized introduction of a large separator drop, thereby preventing problems in detection and data analysis.

Figure 18:
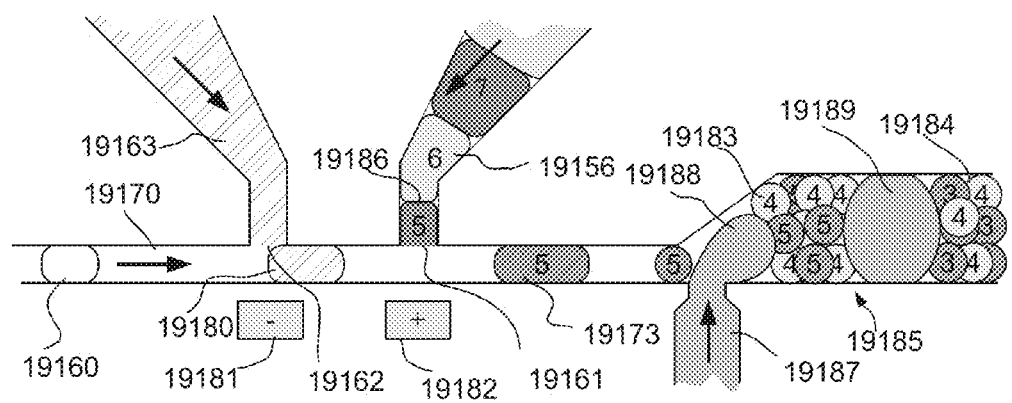

FIG. 18 is an illustration of an example of one embodiment of a system and method where sets of drops downstream from injection sites are prevented from substantially mixing within the channel by a systematic introduction of a large separator drop, thereby preventing problems in detection and data analysis.

Figure 19:
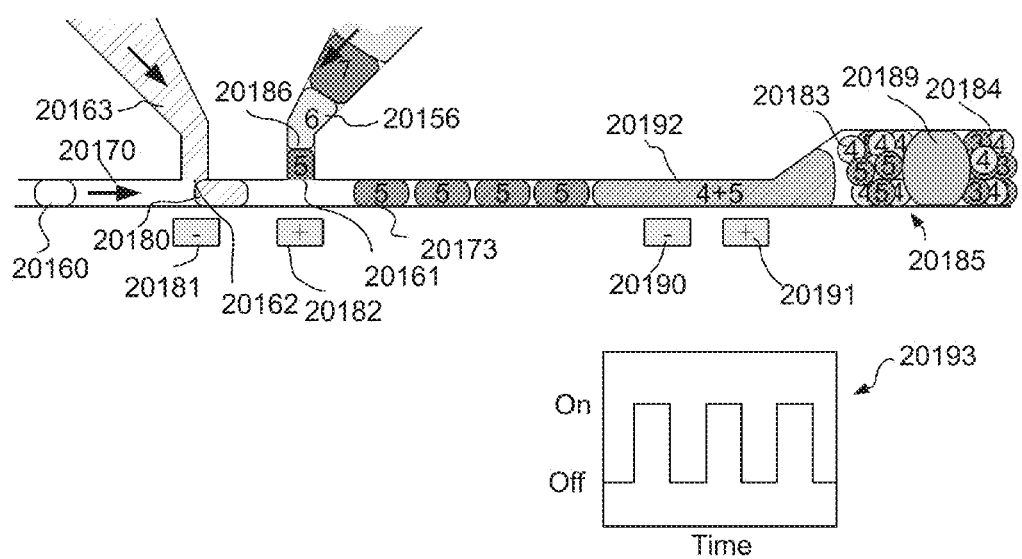

FIG. 19 is an illustration of an example of one embodiment of a system and method where sets of drops downstream from injection sites are prevented from substantially mixing within the channel by a systematic merging sets of drops into a large separator drop using a cycling electric field, thereby preventing problems in detection and data analysis.

DETAILED DESCRIPTION OF THE INVENTION

Figure 1:
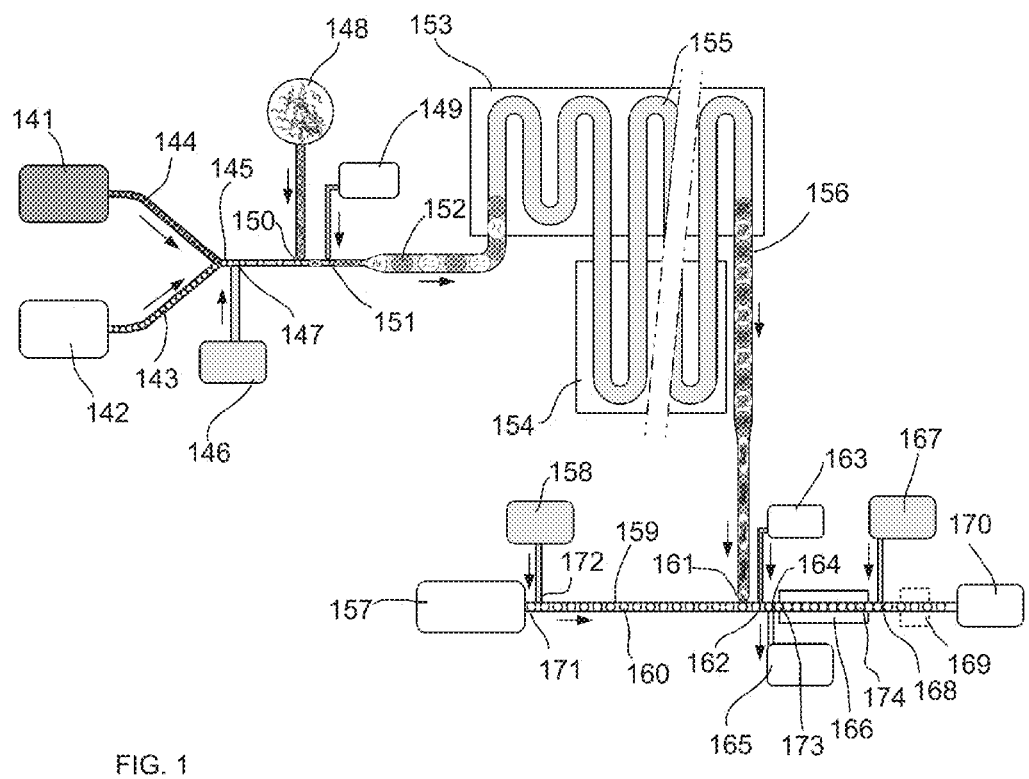
FIG. 1 is an illustration of an example of one embodiment of a microfluidic system, which is performing a cascading assay.

A variety of aspects for use in microfluidic systems are provided herein, including but not limited to methods of interleaving droplets, methods of increasing and decreasing the volume of immiscible fluid in an emulsion (thereby decreasing or increasing the density of droplets, respectively), methods of filtering emulsions, and methods of tracking and/or separating sets of droplets. The methods, devices and systems described herein can be used in isolation or adapted to any number of different microfluidic system configurations. One such system is depicted in FIG. 1. It should be recognized that the system of FIG. 1 is not intended to limit the invention. For example, aspects of the system of FIG. 1 can be used in separation from other aspects of the system while using the inventive configurations described herein.

In one or more embodiments, the system comprises one or more injection inlet. The injection inlet may be of any shape, including but not limited to, circular, elliptical, triangular, rectangular and so forth. The injection inlet may have an average cross-sectional dimension of less than about 1 mm, less than about 100 µm, less than about 10 µm, less than about 1 µm, less than about 100 nm, and so forth. The injection inlet may be flush with the microfluidic channel or, alternatively, may protrude into the microfluidic channel.

The system can further comprise a mechanism for disrupting at least a portion of the interface between a drop flowing in a microfluidic channel and a fluid and/or emulsion in an injection channel, resulting in injection of a relatively controlled volume either into or out of a drop and, hence, a respective increase or decrease in the volume of the drop relative to prior to injection. An "interface", as used herein when referring to the interface between a drop and a fluid and/or emulsion, is one or more region where two immiscible or partially immiscible phases (e.g., a drop and a fluid or emulsion) are capable of interacting with each other. Upon disruption of the interface, there is a relative flow of volume either from the injection channel and into the drop or out of the drop and into the injection channel, all via the injection inlet associated with the particular injection channel. As the drop continues to flow past the injection inlet, there is a shearing force that breaks the contact between the drop and the fluid and/or emulsion, followed by restoration of the interface and end of volume flow between the drop and the fluid and/or emulsion. Droplet injectors (also referred to as "picoinjectors"), i.e., injectors of small amounts of fluid, e.g., from a portion of one drop, into another drop, are described in, e.g., US 2012/0132288 and WO 2012/135259.

In one or more embodiments, the volume injected into or out of each drop may be any suitable amount, depending on the embodiment, as will be appreciated and understood by one of skill in the art. For example, the volume injected into or out of each drop may be less than about 10 µL, less than about 1 µL, less than about 100 nL, less than about 10 nL, less than about 1 nL, less than about 100 pL, less than about 10 pL, less than about 1 pL and so forth.

Exemplary system components are described in, e.g., US2011/0267457, US2011/0151578, US2011/0218123, US2012/0222748, US2011/0218123, 2012/0222748, WO2012/135201, WO2012/135259, WO2014/043388, WO 2012/135327.

The direction and rate of volume may be controlled by controlling various factors of the drops, fluids, emulsions, and/or system components, including but not limited to, the mechanism of disrupting the interface between the drop and the fluid and/or emulsion (discussed further below); the curvature and/or velocity of the drop; the pressure in the injection channel and/or the microfluidic channel relative to one another; the surface tension of the drop; the surface tension of the fluid and/or emulsion; the geometry of the injection inlet, and so forth as will be known and appreciated by one of skill in the art. The above factors may, in some instances, result in forces acting on the system, as described below.

For example, the injection inlet should be constructed such that the pressure of the system may be balanced to substantially prevent the fluid and/or emulsion in the injection channel from flowing into the microfluidic channel unless there is a pressure drop present in the microfluidic channel and in direct contact with an injection interface, and there is sufficient activation energy to foster injection of volume between the drop in the microfluidic channel and the fluid and/or emulsion in an injection channel. Accordingly, when there is no drop in direct contact with an injection interface or, in instances where there is a drop in direct contact with an injection interface but there is no mechanism for disrupting the interface between the drop and a fluid and/or emulsion, there is substantially no net positive or net negative flow of volume into or out of the drop or into or out of an injection channel because the forces pushing volume out of an injection channel and into the drop are substantially balanced by the forces pushing volume out of the drop and into the injection channel. Accordingly, in some embodiments, a system can be constructed to substantially prevent dripping of fluid and/or emulsion from the injection channel into the microfluidic channel when there is no drop in direct contact with an injection interface or, in instances where there is a drop in direct contact with an injection interface but there is no mechanism for disrupting the interface between the drop and a fluid and/or emulsion.

The mechanism for disrupting the interface between a drop and a fluid and/or emulsion may be selected from any passive or active method, or combinations thereof, known and appreciated by one of skill in the art. Xu, et al., "Drop Coalescence in Microfluidic Systems", Micro and Nanosystems (2011) vol. 3, no. 2, pp. 131-136, the entirety of which is incorporated herein by reference, describes many interface disruption mechanisms in the context of drop coalescence but the same apply for injection of multiple substantially controlled volumes into or out of a drop, as will be known, understood and appreciated by one of skill in the art.

Passive methods for disrupting the interface do not require external energy and can rely primarily on the structure and surface properties of the microfluidic channel and associated injection channels and respective injection inlets. Passive methods for disrupting the interface include, but are not limited to, flow trapping and surface modification, which are further described by Xu, et al. and will be known and appreciated by one of skill in the art.

"Inflation," as used herein, refers to increasing the volume or content of a vehicle by injecting or other means of transferring fluid or other components into the vehicle such as by diffusion or osmotic controlled diffusion or, in the case of a sample, refers to increasing the volume of content of a sample to allow for amplification (e.g., PCR, cell division or other mechanism for increasing the content or volume of a sample) such that the size, volume and/or content of the sample or vehicle becomes relatively larger than prior to inflation. "Partitioning," as used herein, refers to dividing, subdividing and/or partitioning of a sample or vehicle such that the size, volume and/or content of the sample or vehicle become relatively smaller than prior to partitioning.

Accordingly, in one example, a sample within a vehicle (e.g., a droplet) may be amplified (e.g., by PCR, cell division or other mechanism for increasing the content of a sample) one, two or multiple times comprising multiple samples and/or partitioned one, two or multiple times into multiple individual samples within a cascading assay. Likewise, in another example, a vehicle containing a sample may be inflated one, two or multiple times and/or partitioned one, two or multiple times into multiple vehicles, wherein each vehicle may comprise one or more samples, within a cascading assay. Moreover, in yet another example, a sample present in a first vehicle may be injected into a second vehicle, wherein the second vehicle may or may not comprise one or more additional samples, within a cascading assay. Additionally, in still another example, a sample may be amplified on the surface of a carrier (e.g., a bead). In this example, the carrier may further be present within a vehicle comprising multiple carriers, wherein each carrier comprises at least one sample on its surface, and wherein each sample is subsequently separated from its respective carrier followed by selective partitioning of one or more samples from one or more other samples as the vehicle is partitioned one or more times, within a cascading assay. In this example, after a sample is separated from its respective carrier, the carrier may or may not be removed from the vehicle as the vehicle is partitioned one or more times.

In one embodiment, the system is an integrated microfluidic device. A "microfluidic device", as used herein, is a device that enables a means of effecting a deterministic function on liquid or gas fluids at small scales typically measured in volumes such as, for example, milliliter (mL), microliter (µL), nanoliter (nL), picoliter (pL), or femtoliter (fL) volumes and/or by physical scale such as millimeter (mm), micrometer (µm) (also referred to as "micron"), nanometer (nm), and so forth. Functions may include mixing, splitting, sorting, heating, and so forth. Microfluidic devices may comprise microfluidic channels as a means for transferring fluids or samples from one point to another and are typically of uniform cross section in the mm, µm or nm scale.

A wide variety of methods and materials exists and will be known and appreciated by one of skill in the art for construction of microfluidic channels and networks thereof, such as those described, for example, in U.S. Pat. No. 8,047,829 and U.S. Patent Application Publication No. 20080014589, each of which is incorporated herein by reference in its entirety. For example, the microfluidic channel may be constructed using simple tubing, but may further involve sealing the surface of one slab comprising open channels to a second flat slab. Materials into which microfluidic channels may be formed include silicon, glass, silicones such as polydimethylsiloxane (PDMS), and plastics such as poly(methyl-methacrylate) (known as PMMA or "acrylic"), cyclic olefin polymer (COP), and cyclic olefin copolymer (COC). The same materials can also be used for the second sealing slab. Compatible combinations of materials for the two slabs depend on the method employed to seal them together. The microfluidic channel may be encased as necessary in an optically clear material to allow for optical excitation (resulting in, e.g., fluorescence) or illumination (resulting in, e.g., selective absorption) of a sample as necessary, and to allow for optical detection of spectroscopic properties of light from a sample, as the sample is flowing through the microfluidic channel. Preferred examples of such optically clear materials that exhibit high optical clarity and low autofluorescence include, but are not limited to, borosilicate glass (e.g., SCHOTT BOROFLOAT® glass (Schott North America, Elmsford N.Y.)) and cyclo-olefin polymers (COP) (e.g., ZEONOR® (Zeon Chemicals LP, Louisville Ky.)).

FIG. 1 is an illustration of an example of one embodiment of a system for performing a cascading assay. In this example, a two-stage integrated emulsion-based microfluidic system is illustrated, wherein the system may be used to perform a cascading assay comprising a first stage and a second stage, as discussed in greater detail below. The system 140 in this example provides for the performance of various functions, including but not limited to, target nucleic acid selection and amplification, assay, detection and data analysis. However, the system, samples and reagents may be modified accordingly to perform any type of assay.

In the first stage of the cascading assay performed by the system depicted in FIG. 1, sample DNA is introduced into a sample vessel 148. PCR primers that are uniquely labeled (e.g., with unique fluorophores) and contained within drops (e.g., primer drops, i.e., drops comprising one or more oligonucleotide primer of different sequence) in the form of an emulsion are introduced into reagent vessels 141 and 142. The primer drops in reagent vessel 141 flow in primer channel 144 and primer drops in reagent vessel 142 flow in primer channel 143. Primer channel 143 intersects with primer channel 144 at microfluidic channel 145. The primer drops flow in primer channels 143 and 144 in a manner such that the primer drops enter microfluidic channel 145 in an alternating manner. DNA polymerase is introduced into reagent vessel 149. Sample vessel 148 and reagent vessel 149 each further comprise selection and amplification reagents and components such as, but not limited to, PCR primers, buffers, dNTPs, and BSA (bovine serum albumin).

In this example, primer drops in reagent vessel 141 are labeled (e.g., fluorescently) differently than those in reagent vessel 142 such that the labels may be monitored at a final detection stage. Upon entering microfluidic channel 145, the primer drops are spaced relatively uniformly with oil from vessel 146 (or, alternatively, any fluid capable of maintaining drop separation). This results in relatively uniformly spaced primer drops 147, wherein the primer drops 147 are spaced at a relatively uniform distance at a particular flow rate. Each of the uniformly spaced primer drops 147 are first injected with sample from sample vessel 148 by way of the sample vessel injector 150, followed by injection with DNA polymerase from reagent vessel 149 by way of the reagent injector 151.

This process results in the formation of relatively larger drops 152, wherein each drop comprises sample DNA, primers and PCR reagents, flowing within the microfluidic channel 145.

The drops 152 next flow through a serpentine-like microfluidic channel 155 while repeatedly passing through two temperature zones, first temperature zone 153 and second temperature zone 154, respectively, as part of the process of undergoing PCR amplification of the sample DNA. First temperature zone (denaturation temperature zone) 153 allows for the denaturing of the sample DNA. Alternatively, the system may be modified to allow for a three-step PCR process whereby the sample DNA is PCR amplified by being subjected to multiple controlled temperature zones within the system, as will be understood and appreciated by one of skill in the art. As the drops 152 flow through the serpentine-like microfluidic channel 155, they pass through alternating temperature zones 153 and 154 as part of the PCR process resulting in PCR product drops 156 comprising PCR-amplified sample DNA.

The system illustrated in FIG. 1 further comprises a DNA probe drop vessel 157 comprising a library of DNA probes contained within drops. Drops comprising DNA probes (probe drops) 160 are injected from DNA probe drop vessel 157 by way of DNA probe drop injector 171, which intersects with microfluidic channel 159. As the probe drops 160 are injected into microfluidic channel 159, they are relatively uniformly spaced by oil injected from oil vessel 158 by way of oil injector 172.

In the second stage of the cascading assay performed by the system depicted in FIG. 1, as the PCR products drops 156 flow through the serpentine-like microfluidic channel 155, a portion or all of each individual PCR product drop 156 may be injected into one or more probe drops 160 flowing in microfluidic channel 159 by way of injector 161 at the point at which the serpentine-like microfluidic channel 155 intersects with microfluidic channel 159. Next, the probe drops 160 are injected with detection assay reagents (e.g., reagents for a sequencing reaction, including but not limited to a hybridization-based sequencing reaction) from reagent vessel 163 by way of reagent vessel injector 162. Alternatively, the system 140 in this example may be modified such that the order of injection may be reversed, i.e., the detection assay reagents are injected into the probe drops 160 prior to injection of PCR product drops 156. In this example, electrodes (not shown) provide a mechanism for disrupting the interface between the probe drops 160 and a fluid and/or emulsion comprising the material (PCR product drops and detection assay reagents, in this example) being injected into the probe drops 160. Despite the order of injection, the result is drops comprising probe plus amplified sample, referred to herein as pre-incubation drops 173.

In one embodiment, hybridization is detected as described in WO 2012/078710, which is incorporated herein by reference in its entirety. Briefly, this method can involve generating a target nucleic acid amplicon comprising florescent label or other detectable substance, e.g., a nucleic acid sequence covalently-linked fluorescent label, and annealed to an inhibitor polynucleotide comprising a quencher such that hybridization of the inhibitor polynucleotide to the target nucleic acid results in quenching of the fluorescent label signal. The detector nucleic acid (i.e., the sequence associated with the target to which the inhibitor polynucleotide hybridizes) can be part of the target sequence amplicon or can be added to the target nucleic acid sequence. A test primer (i.e., one or more primer in a reaction partition) within the probe drops (160) can be combined with the target nucleic acid/inhibitor polynucleotide duplex from a PCR product drop (156) and a strand displacing polymerase (e.g., from 163) such that if the primer anneals to the target nucleic acid, the polymerase extends the primer and displaces the inhibitor polynucleotide, thereby generating a fluorescent signal, indicating that the primer has hybridized. If the primer does not hybridize, the quencher is not displaced and no (or reduced) signal is detected. Note, in an alternative configuration, the quencher and fluorescent label can also be linked to the target nucleic acid and the inhibitor polynucleotide, respectively. The strand displacement assay can occur isothermally and thus does not require thermocycling. In some embodiments, the target nucleic acid will be generated as an amplicon, having a 5' fluorescent label and optionally, a 3' stem (i.e., double stranded end formed by hybridization of an oligonucleotide to the 3' end) or stem loop.

Excess oil may be removed from microfluidic channel 159 by an oil remover 164 and collected in waste vessel 165. Removing excess oil allows for tight packing as the pre-incubation drops 173 next pass through incubation temperature zone 166 while flowing in a relatively uniform manner allowing for each drop to undergo relatively the same amount of incubation time and to remain a member of a collective unit of pre-incubation drops 173 as opposed to receiving a variable incubation time or straying from the other pre-incubation drops. The temperature of incubation temperature zone 166 may comprise one, two or multiple temperatures; one, two or multiple temperature gradients; one, two or multiple temperature cycles, or any combination of the above. Following incubation, the drops are referred to as post-incubation drops 174, which then pass through the temperature zone 166 in a relatively uniform manner by being spaced with oil from oil vessel 167 via oil injector 168. The relatively uniform spacing of the probe drops 160 must be sufficient to separate the post-incubation drops 174 for individual detection and analysis by the detector 169 and the user. After detection, the post-incubation drops 174 are collected in a waste well 170.

In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets.

Methods and compositions for partitioning (e.g., forming droplets from) a sample are described, for example, in published patent applications WO 2010/036352, US 2010/0173394, US 2011/0092373, US 2011/0092376, US2012/0222748; WO2013/09573; and US 2011/0218123 the entire content of each of which is incorporated by reference herein.

In some embodiments, the droplet is formed by flowing an oil phase through an aqueous solution comprising the label(s) to be detected. In some embodiments, the aqueous sample comprising the label(s) to be detected comprises a buffered solution and reagents for detecting the label(s). The oil for the oil phase may be synthetic or naturally occurring. In some embodiments, the oil comprises carbon and/or silicon. In some embodiments, the oil comprises hydrogen and/or fluorine. Exemplary oils include, but are not limited to, silicone oil, mineral oil, fluorocarbon oil, vegetable oil, or a combination thereof.

The oil phase may comprise a fluorinated base oil which may additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

Systems, Devices, and Methods of Interleaving Droplets

In some aspects, systems and reagents for performing a method for interleaving (adding in alternating order) two previously formed populations of drops containing samples of interest in a substantially alternating fashion are provided. In some embodiments, methods and systems to label a portion of previously formed population of drops and then interleaving the labeled and unlabeled drops in a substantially alternating fashion are provided. In some embodiments, a system comprises a microfluidic device capable of producing a train or succession of alternating drops. In some aspects, the system and method provide for the alternating flow of differentially labeled drops by way of passive hydrodynamic forces without the need for a computer, optical detector or other active control mechanism, thus providing a more simple and efficient alternative to known techniques.

Figure 2:
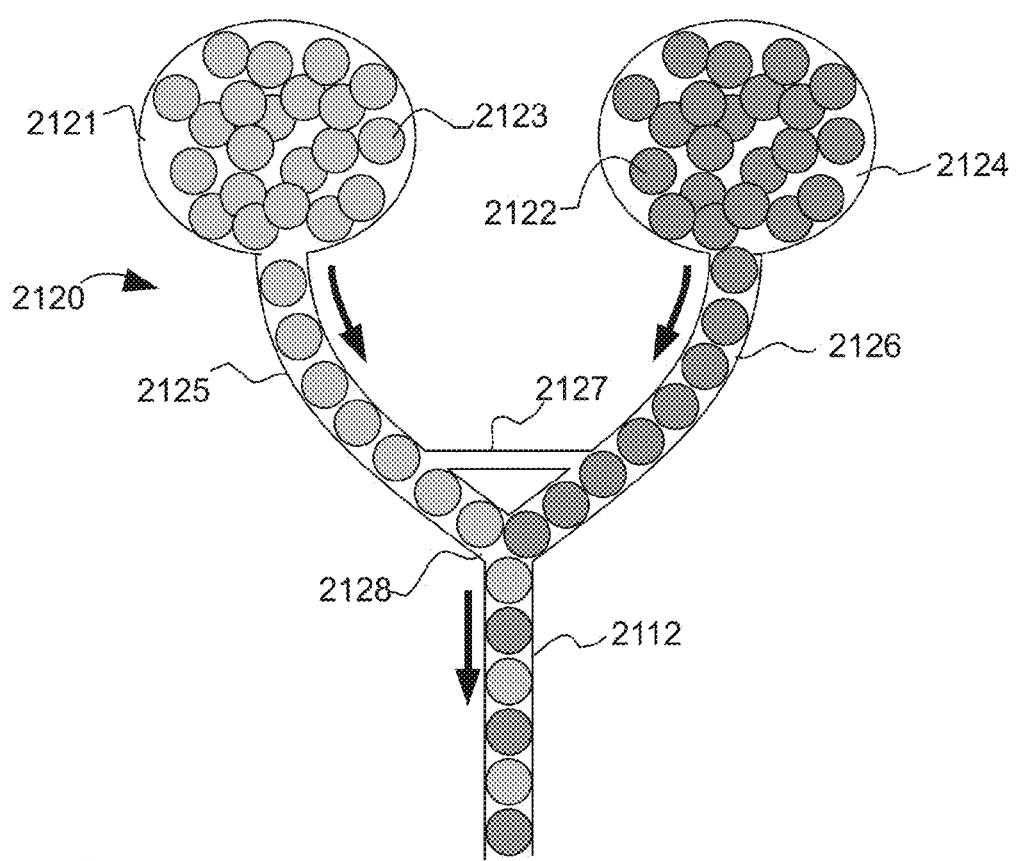
FIG. 2 illustrates an example of one embodiment comprising of a microfluidic device for interleaving two previously formed emulsions in a substantially one-by-one alternating fashion.

The system and method described herein results in a train of droplets that alternate between droplets of two different detectable states, wherein said detectable states refer to, for example, differences in the color of a droplet or differences in the intensities of a particular color from one droplet to the next. FIG. 2 is an illustration of an example of the system (2120), wherein the system is comprised of a microfluidic device with two inlets for differently labeled droplets (2121 and 2124). The two differentially labeled drop populations (2123 and 2122) flow along channels (2126 and 2125) towards a junction (2128). Upstream of this junction (2128), is an optional connection channel (2127) which allows a continuous phase fluid to flow between the channels (2125 and 2126), and is sized so that the droplets are too large to enter the channel. After the junction (2128), the two differentially labeled droplet populations are interleaved in a substantially one-by-one alternating fashion, in a joint microfluidic channel (2112). The embodiment in FIG. 2 occurs, for example, in FIG. 1, items 141-145.

Figure 3:
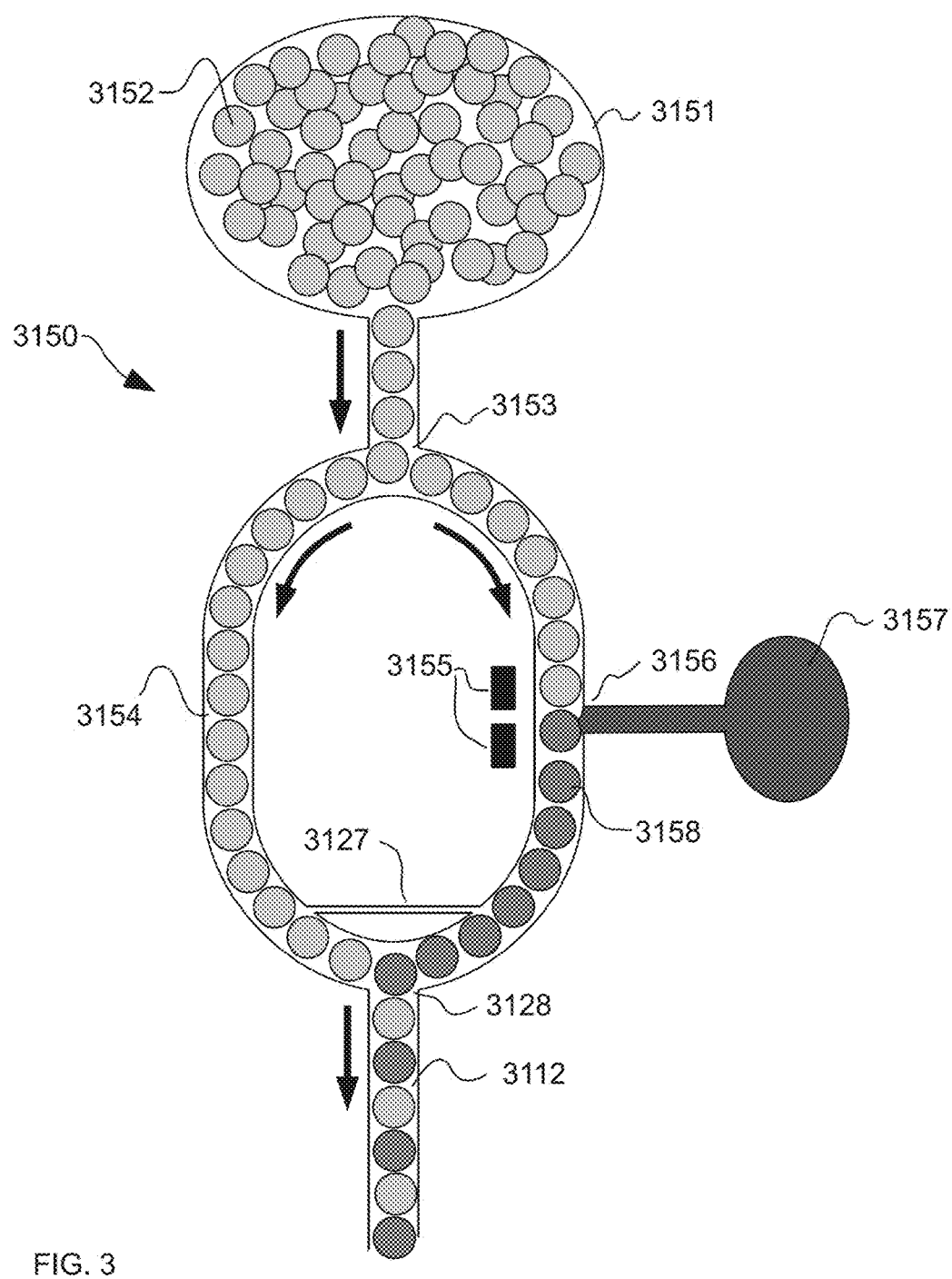
FIG. 3 illustrates an example of one embodiment according to the present invention comprising of a microfluidic device for selectively labeling a portion of previously formed drops and then for interleaving the labeled drops with the unlabeled portion of the population in a substantially one-by-one alternating fashion.

Referring to FIG. 3, which is an illustration of an example of the system (3150), according to the present invention, wherein the system is comprised of a microfluidic device in which half of an initially homogeneous population of droplets in inlet (3151) are marked with a label (3157), at the junction (3156). This labeling is done through a process which disrupts the interface between the immiscible label (3157) and the continuous phase, for example by the use of an applied electric field via electrodes (3155). For the case where the interface between the immiscible label (3157) and the droplets at junction (3156) is interrupted by an electric field, the droplets approaching junction (3156) can be spaced so that neighboring droplets do not coalesce due to the presence of the electric field. The labeled droplets (3158) and the unlabeled droplets flow downstream towards a junction (3128) where they are interleaved in a one-by-one alternating fashion, in a joint microfluidic channel (3112).

Any sort of label can be used, as appropriate. Labels can include, for example, molecules that scatter light, emit light as chemilluminescence (e.g., by a chemical process), selectively absorb light, or emit light as fluorescence (e.g., following excitation). Label can be inserted into a droplet by disrupting the continuous phase (e.g., oil)/droplet interface in the presence of the label, thereby inserting the label into the droplet. The mechanism for disrupting the continuous phase/droplet interface may be selected from any passive or active method, or combinations thereof, known and appreciated by one of skill in the art. Xu, et al., "Droplet Coalescence in Microfluidic devices", Micro and Nanomicrofluidic devices (2011) vol. 3, no. 2, pp. 131-136, the entirety of which is incorporated herein by reference, describes many interface disruption mechanisms in the context of droplet coalescence but the same apply for inflation of droplets with multiple substantially controlled volumes of fluid, as will be known, understood and appreciated by one of skill in the art.

Passive methods for disrupting the continuous phase/droplet interface do not require external energy and rely primarily on the structure and surface properties of the microfluidic channel and associated inflators and respective inflator nozzles. Passive methods for disrupting the interface include, but are not limited to, flow trapping and surface modification, which are further described by Xu, et al. and will be known and appreciated by one of skill in the art.

Examples of passive methods for disrupting the continuous phase/droplet interface include, but are not limited to, the use of a localized hydrophilic region in a microfluidic channel, wherein the microfluidic channel comprises hydrophobic walls and contains aqueous based droplets in a continuous oil phase flowing therein. The hydrophobic walls of the microfluidic channel prevent wetting of droplets and promote the presence of a thin layer of the continuous phase between the droplets and the microfluidic channel surface. However, when the microfluidic further comprises a localized region that is relatively hydrophilic, wetting of the droplets occurs as they flow pass this localized region, resulting in disruption of the previously stable interface and inflation of fluid into the droplet. Once the droplets flow past this localized region, the continuous phase will naturally re-wet the microfluidic channel wall and, thus, promote reformation and stabilization of the droplets. A localized hydrophilic region may be created in a hydrophobic microfluidic channel by various methods known and appreciated by one of skill in the art, including but not limited to, constructing the microfluidic channel with a material having surface chemistry that may be initiated with ultraviolet (UV) light, such that shining UV light to the localized region will induce said surface chemistry resulting in a change in the material surface property of the region from relatively hydrophobic to relatively hydrophilic.

Other examples of passive methods for disrupting continuous phase/droplet interface include creating posts or other disruptions in the path of the droplet intended to increase the shear forces on the droplet as it passes through a particular region of the microfluidic channel, or, alternatively, incorporating valves into or deformations in the walls of the microfluidic channel to physically trap a droplet to promote destabilization of at least a portion of the interface. Each of these methods results in a relatively unstable interface which, as described above, reforms and stabilizes once the droplet passes the region of disruption.

Active methods for disrupting the continuous phase/droplet interface require energy generated by an external field. Active methods for disrupting the interface include, but are not limited to, electrocoalescence (i.e., by applying an electric field through the use of, e.g., one or more pairs of electrodes either in contact with the fluids or external to them) and dielectrophoresies (DEP), temperature and pneumatically actuated methods, including the use of lasers and acoustic pressure methods, many of which are described by Xu, et al. and will be known and appreciated by one of skill in the art.

Examples of active methods for disrupting the continuous phase/droplet interface include, but are not limited to, changing the temperature in a localized region of the microfluidic device, resulting in temperature-dependent viscosity and surface tension changes affecting disruption of the interface between a droplet and a fluid and/or emulsion. For example, a laser may be focused (in the form of a "laser spot") on a region of the microfluidic channel encompassing an inflation interface. Such spatial variation in temperature around the laser spot will promote spatial imbalance of droplet surface tension, resulting in a thermocapillary effect on and, hence, destabilizing of, the interface. In another example, acoustic pressure waves may be used to disrupt the surface of a droplet, change the wettability of a droplet or manipulate the position of a droplet. As with methods discussed previously, each of these methods results in a relatively unstable interface which, as described above, reforms and stabilizes once the droplet passes the region of disruption.

In one or more embodiments, the mechanism for disrupting the continuous phase/droplet interface is selected from at least one pair of electrodes. In such embodiments, the at least one pair of electrodes may be positioned substantially orthogonal to the microfluidic channel. In some aspects of one or more embodiments, the at least one pair of electrodes may be positioned substantially opposite to one or more inflator. The at least one pair of electrodes applies an electric field to one or more inflation interface. In some examples, the at least one pair of electrodes may be positioned such that the electrodes create an electric field maximally located within one or more inflation interface or at least proximate to the inflation interface.

In embodiments wherein at least one pair of electrodes is utilized as a mechanism for disrupting the interface between the continuous phase/droplet interface as described above, the electrodes may be positioned in a variety of configurations relative to other components of the microfluidic device. For example, a first electrode and a second electrode of at least one pair of electrodes may be positioned above or below the microfluidic channel. In some instances, a first electrode and a second electrode of at least one pair of electrodes may be positioned essentially on opposite sides of the microfluidic channel. In other instances, a first electrode and a second electrode of at least one pair of electrodes may be positioned essentially on opposite sides of both the microfluidic channel and one or more inflators. In yet other instances, a first electrode and a second electrode of at least one pair of electrodes may be positioned such that a plane intersects both electrodes. In still other instances, a first electrode and a second electrode of at least one pair of electrodes may be positioned to be co-planar with the microfluidic channel and/or co-planar with one or more inflator and/or co-planar with one or more inflator nozzle, such that the electrodes are positioned such that a plane intersects with each of these. In still another aspect of this embodiment, only one of the electrodes in a particular pair of electrodes needs to be localized. For example, a large ground plane may serve many individual, localized electrodes. In another example, a continuous phase fluid (which may or may not be the fluid in the inflation channel) may serve as one of the electrodes in a pair.

The electrodes may be fabricated from any suitable material, which will be understood and appreciated by one of skill in the art. For example, the electrodes may be fabricated from materials including, but not limited to, metals, metalloids, semiconductors, graphite, conducting polymers, and liquids, including but not limited to ionic solutions, conductive suspensions, liquid metals, and so forth. The electrodes may have any shape suitable for applying an electric field, as will be understood and appreciated by one of skill in the art. For example, an electrode may have an essentially rectangular shape. In this example, the electrode may be elongated and have a tip defined as a region of the electrode closest to an inflation interface. The electrode tip is constructed such that a sufficient electric field is created in said intersection or substantially proximate to an inflation interface as described previously.

In some examples where more than one pair of electrodes is employed, the electrodes may be constructed to minimize interference between one or more electrodes and one or more inflators, for example, by minimizing the unintended exposure of a first interface to an electric field by an electrode intended to expose a second interface positioned in a different location than the first interface to an electric field. In some aspects, this may be accomplished by reducing the size of the electrode tip to allow more focused application of an electric field by the electrode tip such that one or more interfaces are not unintentionally exposed to the electric field, and/or are exposed to relatively lower electric field strengths. In other aspects, the region comprising an inflator and respective inflator nozzle may be modified, e.g., by adding dimension in the form of a small bump or other modification for the purpose of localizing and strengthening the electric field in that around an inflation interface. Such aspects of the present invention may be advantageous, for example, in instances where it is desired to reduce the distance between multiple microfluidic channels, each associated with multiple inflators and respective inflator nozzles as part of a microfluidic device.

Aspects of microfluidic manipulation of droplets are described in US Patent Publication No. 2011/0264757 and PCT Publication No. WO2014/043388, and references cited therein, are each incorporated by reference. Non-limiting examples of microfluidic systems that may be used with the present invention are disclosed in U.S. patent application Ser. No. 11/246,911, filed Oct. 7, 2005, entitled "Formation and Control of Fluidic Species," published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion," published as U.S. Patent Application Publication No. 2005/0172476 on Aug. 11, 2005; U.S. patent application Ser. No. 11/360,845, filed Feb. 23, 2006, entitled "Electronic Control of Fluidic Species," published as U.S. Patent Application Publication No. 2007/000342 on Jan. 4, 2007; International Patent Application No. PCT/US2006/007772, filed Mar. 3, 2006, entitled "Method and Apparatus for Forming Multiple Emulsions," published as WO 2006/096571 on Sep. 14, 2006; U.S. patent application Ser. No. 11/368,263, filed Mar. 3, 2006, entitled "Systems and Methods of Forming Particles," published as U.S. Patent Application Publication No. 2007/0054119 on Mar. 8, 2007; U.S. Provisional Patent Application Ser. No. 60/920,574, filed Mar. 28, 2007, entitled "Multiple Emulsions and Techniques for Formation"; and International Patent Application No. PCT/US2006/001938, filed Jan. 20, 2006, entitled "Systems and Methods for Forming Fluidic droplets Encapsulated in Particles Such as Colloidal Particles," published as WO 2006/078841 on Jul. 27, 2006, each incorporated herein by reference in their entireties.

Controlled Change in the Continuous Phase of an Emulsion

In some aspects, systems, methods and kits for performing a controlled change in the continuous phase volume fraction from an emulsion in a microfluidic device are provided. One embodiment of the system pertains to a microfluidic device for performing a controlled change in the continuous phase volume fraction from an emulsion. The microfluidic devices can comprise one or more microfluidic channels as a way for transferring droplets, fluids and/or emulsions from one point to another point and one or more relatively smaller (e.g., smaller than the average diameter of droplets in the microfluidic channel) extraction channels or membranes connected to and in communication with one or more microfluidic channels. For example, microfluidic channels can carry droplets of about 10-30 µm in diameter and comprises smaller extraction channels of 1-10 µm wide cross section, e.g., 2-6 µm. In one aspect of this embodiment, the one or more extraction channels or oil-permeable membranes are a way for extracting continuous phase volume fraction from the one or more microfluidic channels and transferring the continuous phase volume fraction into another one of the one or more microfluidic channels. In some aspects, a method is provided for performing the controlled change in the continuous phase volume fraction from an emulsion in a microfluidic device, as described previously and further herein. Aspects described in this section can be included, for example, in a system as depicted in FIG. 1 at items 146-147 or 164-165.

The microfluidic devices of these aspects can comprise one or more microfluidic channels for transferring droplets, fluids and/or emulsions from one point to another point and one or more relatively smaller extraction channels connected to and in communication with one or more microfluidic channels and wherein the one or more extraction channels are a means for extracting emulsion from the one or more microfluidic channels and transferring said emulsion into another one of the one or more microfluidic channels.

The emulsions (including a continuous phase and a dispersed phase comprised therein, wherein the dispersed phase may comprise one or more droplets) can flow through a microfluidic channel by being acted upon by a source of positive or negative pressure, e.g., a pressurized or evacuated air reservoir, syringe pump, gravity or centripetal forces, wherein the pressure source comprises any fluid or combinations of fluids, including but not limited to, any gas or combination of gases (e.g., air, nitrogen, carbon dioxide, argon, and so forth) or any liquid or combinations of liquids (e.g., water, buffer, oil, and so forth), such that the emulsions and droplets flow or stream through a microfluidic channel and are herein referred to as "flowing emulsions (or droplets)" or "streaming emulsions (or droplets)". In some embodiments, the size (or diameter) of the microfluidic channel is sufficiently narrow such that droplets flow through the microfluidic channel in substantially single file.

In some embodiments, the system comprises a microfluidic device. In one aspect of this embodiment, the microfluidic device comprises a first microfluidic channel arranged at any angle to one or more additional microfluidic channels. In one example, a first microfluidic channel is arranged substantially parallel to a second microfluidic channel. In some embodiments, it may be useful for one or more microfluidic channels to be encased in an optically clear material. In one embodiment, one or more microfluidic channels each comprise one or more inlets through which an emulsion enters and one or more outlets through which continuous phase exits.

In one embodiment of the system, the system comprises a microfluidic device comprising a first microfluidic channel and a second microfluidic channel each connected by and in communication with one or more extraction channels or membranes arranged substantially perpendicular to both the first microfluidic channel and the second microfluidic channel. In one aspect of this embodiment, the second microfluidic channel is controllably pressurized such that when an emulsion is introduced into the microfluidic device, a controlled volume fraction of continuous phase flows out of the first microfluidic channel, through the one or more extraction channels or membranes and into the second microfluidic channel, whereas the dispersed phase of the emulsion (e.g., droplets and some continuous phase (e.g., oil)) remains in the first microfluidic channel.

In another embodiment, the microfluidic device comprises multiple (i.e., three or more) microfluidic channels connected by more than one set of extraction channels or membranes. In still another embodiment, the extraction channels or membranes are arranged at an angle other than substantially perpendicular to one or more microfluidic channels. In yet another embodiment, two or more microfluidic channels are arranged at an angle or position other than substantially parallel to each other. In still another embodiment, the one or more microfluidic channels are in the form of a concentric tube comprising small holes or membrane surface along the inner aspect of the tube.

In one embodiment of the system, an emulsion comprising droplets dispersed therein is introduced into a first microfluidic channel and flows through the first microfluidic channel by being pumped or pushed by a pressure source as described above. The pressure of a second microfluidic channel allows continuous phase to flow from the first microfluidic channel into the second microfluidic channel by way of relatively smaller extraction channels or membranes, without substantially removing continuous phase droplets from the first microfluidic channel. In one example, the pressure in the second microfluidic channel is reduced below that of the first microfluidic channel, such that a flow of continuous phase into the second microfluidic channel is generated. However, in this example, the droplets remain in the first microfluidic channel because the pressure difference between the first and second microfluidic channels is not large enough to force dispersed phase droplets through the relatively smaller extraction channels or membranes. The result is an emulsion with a lower volume fraction of continuous phase relative to the emulsion prior to being introduced into the microfluidic device.

The inlet and outlet of each microfluidic channel, extraction channel or membrane may be of any shape, including but not limited to, circular, elliptical, triangular, rectangular and so forth. The outlet may have an average cross-sectional dimension, for example, of less than about 1 mm, less than about 100 µm, less than about 10 µm, less than about 1 µm, less than about 100 nm, less than about 10 nm, and so forth.

Figure 4:
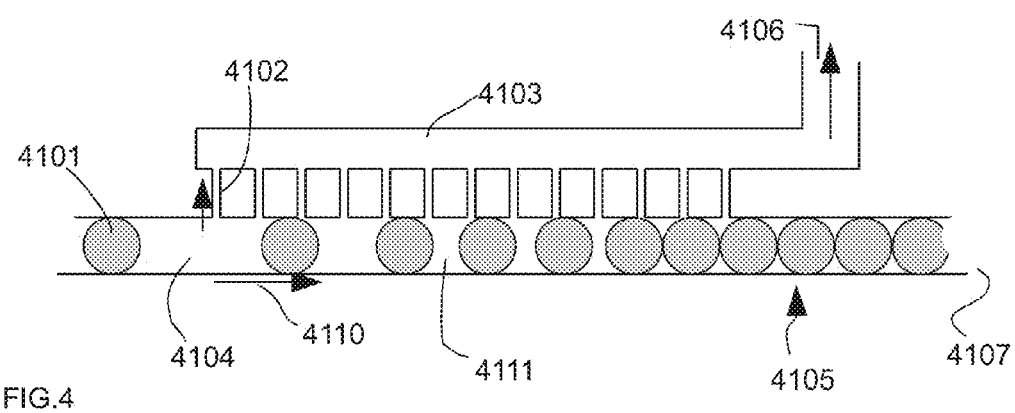
FIG. 4 illustrates a one-sided view of one embodiment of the system in use for performing a controlled change in the continuous phase volume fraction from an emulsion in a microfluidic device incorporating the use of small channels.

In one or more embodiments, the particular volume of a controlled change in the continuous phase volume fraction from an emulsion is any suitable amount, depending on the embodiment. For example, the volume of the controlled change in the continuous phase volume fraction from an emulsion may be about or less than 0.1%, 1%, 5%, 10% oil to drop phase FIG. 4 is an illustration of an example of one embodiment of a microfluidic device for performing a controlled change in the continuous phase volume fraction from an emulsion. More particularly, FIG. 4 illustrates a microfluidic device 4100 wherein dispersed phase droplets (4101, collectively) flow in substantially single file in a first microfluidic channel 4104, separated by continuous phase 4111 in a flow direction 4110. In this example, the first microfluidic channel 4104 is in relatively parallel orientation to a second microfluidic channel 4103. However, as discussed previously, one or more microfluidic channels may be employed in any orientation to each other. The first microfluidic channel 4104 and the second microfluidic channel 4103 are connected to and in communication with, in this example, a series of extraction channels (4102, collectively) (which may be substituted for membranes in alternative examples) connected to one side of each of the first microfluidic channel 4104 and the second microfluidic channel 4103. In this example, the series of extraction channels 4102 are arranged substantially parallel to each other and substantially perpendicular to the first microfluidic channel 4104 and the second microfluidic channel 4103. However, as discussed previously, one or more extraction channels may be employed in any orientation to each other and to one or more microfluidic channels. In the example illustrated in FIG. 4, the extraction channels 4102 appear in relatively parallel orientation to each other and in relatively perpendicular orientation to each of the first microfluidic channel 4104 and the second microfluidic channel 4103.

The microfluidic device 4100 is operated by setting the pressure (and, as such, controlling the flow rate) at the outlet 4106 of the second microfluidic channel 4103 such that the pressure at the outlet 4106 is lower than the pressure at the outlet 4107 of the first microfluidic channel 4104. Accordingly, the continuous phase 4111 may flow through the extraction channels 4102 and the second microfluidic channel 4103 without shearing the dispersed phase droplets 4101 or deforming them.

The width of the extraction channels 4102 is chosen to be sufficiently smaller than the diameter of the dispersed phase droplets 4101. For example, in some embodiments, the width or cross section of the extraction channel is 0.5, 0.25, 0.2, 0.1, 0.01 or less than the diameter of the drop. The pressure difference between the first microfluidic channel 4104 and the second microfluidic channel 4103 is selected to prevent dispersed phase droplets 4101 from flowing through the extraction channels 4102. The width of second microfluidic channel 4103 is chosen to be relatively large to avoid high hydrodynamic resistance and, consequently, high pressure at the outlet 4106 of the second microfluidic channel 4103. When dispersed phase droplets 4101 flow past the extraction channels 4102, a fraction of the continuous phase 4111 passes through the extraction channels 4102, reducing the fraction of continuous phase in the first microfluidic channel 4104 and reducing the distance separating the droplets. This results in the formation of a relatively packed emulsion 4105 in the first microfluidic channel 4104, enabling the selection and maintenance of a particular continuous phase volume fraction in a microfluidic device.

Figure 5:
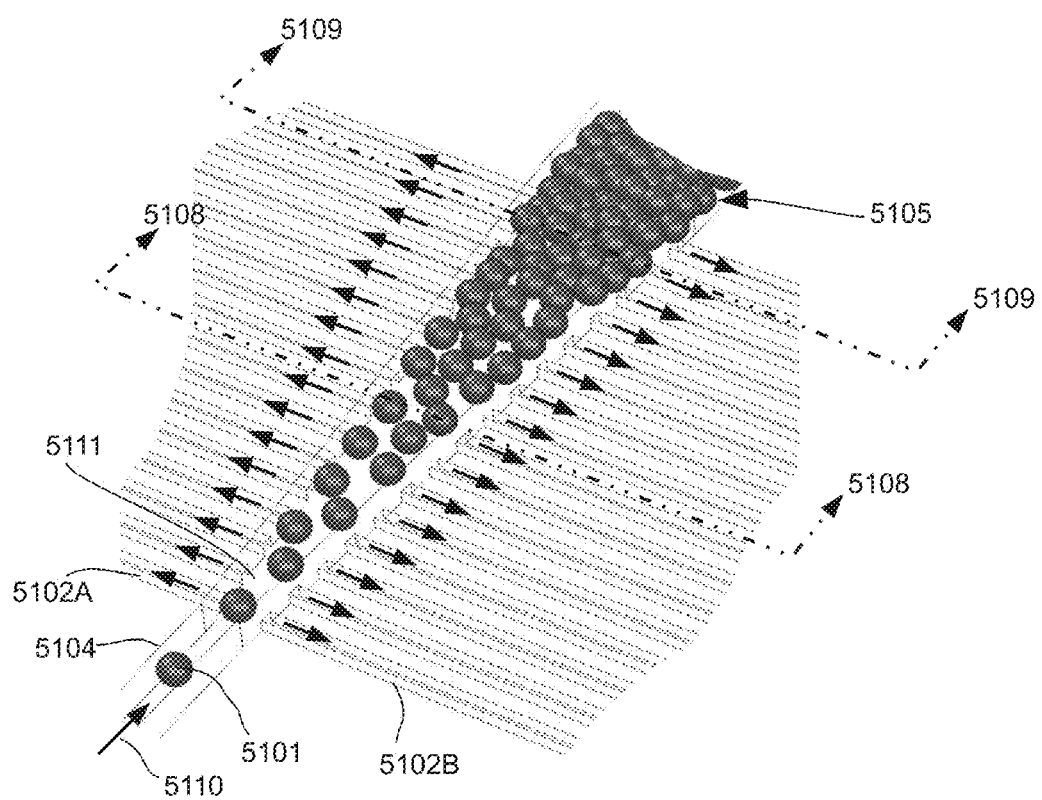
FIG. 5 illustrates a three-dimensional view of one embodiment of the system in use for performing a controlled change in the continuous phase volume fraction from an emulsion in a microfluidic device.

FIG. 5 is a three-dimensional illustration of another example of a system for performing a controlled change in the continuous phase volume fraction from an emulsion in a microfluidic device, according to the present invention. More particularly, FIG. 5 illustrates a three-dimensional view of one embodiment of a microfluidic device 5130 where continuous phase is extracted from substantially opposing sides of the first microfluidic channel 5104. In this example, continuous phase 5111 is extracted from an emulsion by way of two sets of extraction channels (illustrated collectively as 5102A and 5102B for the respective corresponding side of the first microfluidic channel 5104 within the microfluidic device 5130), however, the dispersed phase droplets 5101 are not drawn into either set of channels 5102A or 5102B. Rather, the dispersed phase droplets 5101 continue to flow in flow direction 5110 through the first microfluidic channel 5104 to form a relatively packed emulsion 5105, whereby the packing occurs more tightly as continuous phase is extracted progressively through the microfluidic device 5130. As the first microfluidic channel 5104 intersects with the consecutive extraction channels within extraction channel sets 5102A and 5102B, the first microfluidic channel 5104 gradually widens, resulting in packing of the emulsion with variable droplets velocities due to the presence of a Poiseuille flow. The progressive extraction of continuous phase 5111 via extraction channel sets 5102A and 5102B reduces the continuous phase volume fraction in the emulsion flowing in the first microfluidic channel 5104, resulting in a relatively packed emulsion 5105 occupying the larger portion of cross section 5109 compared to that occupied of cross-section 5108.

Figure 6:
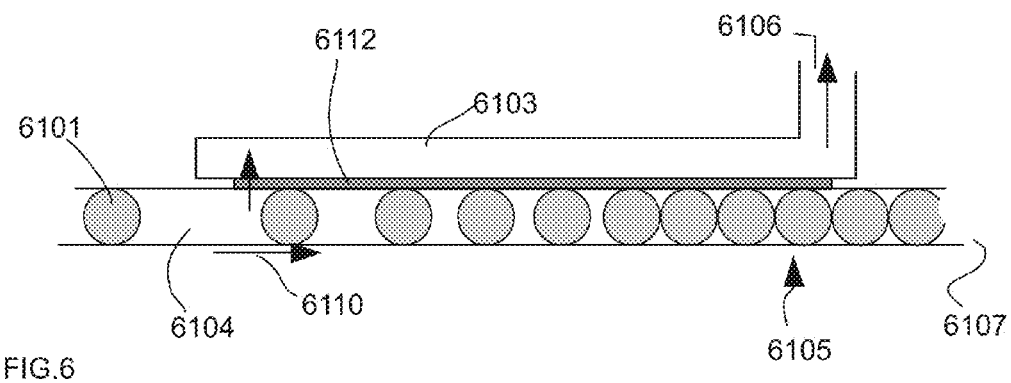
FIG. 6 illustrates a one-sided view of one embodiment of the system in use for performing a controlled change in the continuous phase volume fraction from an emulsion in a microfluidic device incorporating the use of a membrane.

FIG. 6 is an illustration of an example of one embodiment of a microfluidic device for performing a controlled change in the continuous phase volume fraction from an emulsion, according to the present invention. More particularly, FIG. 6 illustrates a microfluidic device 6140 wherein dispersed phase droplets (6101, collectively) flow in substantially single file in a first microfluidic channel 6104 in flow direction 6110 as illustrated. In this example, the first microfluidic channel 6104 is in relatively parallel orientation to a second microfluidic channel 6103. The first microfluidic channel 6104 and the second microfluidic channel 6103 are connected to and in communication with, in this example, a membrane 6112 (which may be substituted for extraction channels in alternative examples, as discussed above) connected to one side or more sides of each of the first microfluidic channel 6104 and the second microfluidic channel 6103. In this example, the membrane 6112 is substantially perpendicular to the first microfluidic channel 6104 and the second microfluidic channel 6103.

Figure 7:
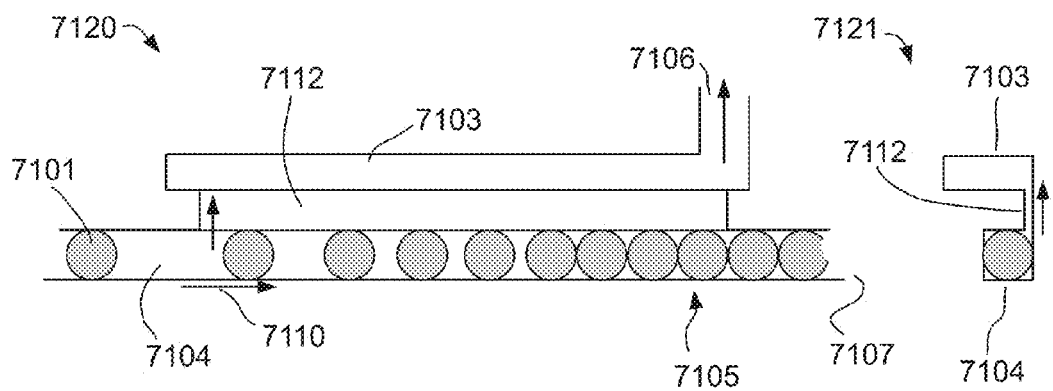
FIG. 7 illustrates a one-sided view of one embodiment of the system in use for performing a controlled change in the continuous phase volume fraction from an emulsion in a microfluidic device incorporating the use of a wide low profile channel.

FIG. 7 is an illustration of an example of one embodiment of a microfluidic device for performing a controlled change in the continuous phase volume fraction from an emulsion, according to the present invention. More particularly, FIG. 7 illustrates a microfluidic device 7140 wherein dispersed phase droplets (7101, collectively) flow in substantially single file in a first microfluidic channel 7104 in flow direction 7110 as illustrated. In this example, the first microfluidic channel 7104 is in a parallel or relatively (e.g., less than 20°, with 0° being parallel) parallel orientation to a second microfluidic channel 7103. The first microfluidic channel 7104 and the second microfluidic channel 7103 are connected to and in communication with, in this example, a wide low profile channel 7112 (which may be substituted for extraction channels in alternative examples, as discussed above) connected to one side or more sides of each of the first microfluidic channel 7104 and the second microfluidic channel 7103. In this example, the height of the wide low profile channel 7112 is substantially smaller (e.g., 0.5, 0.25, 0.2, 0.1, 0.05, 0.01 or less) than the drop 7101 diameter such that the drop is not drawn into the channel 7112.

Figure 8:
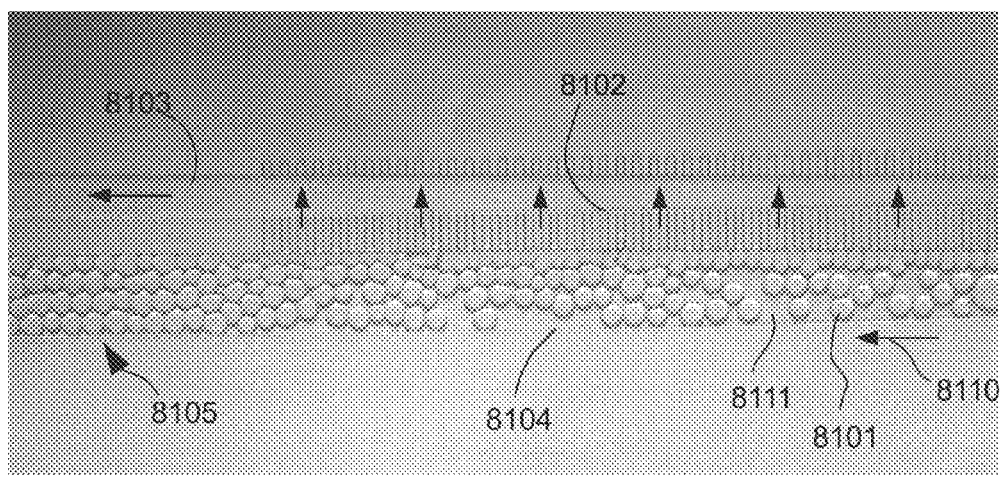
FIG. 8 is a bright field micrograph illustrating an example of an embodiment of a one-sided example of the system in use for performing a controlled change in the continuous phase volume fraction from an emulsion in a microfluidic device.

FIG. 8 is a bright field micrograph illustrating an example of an embodiment of a system in use for performing a controlled change in the continuous phase volume fraction from an emulsion in a microfluidic device, according to the present invention. More specifically, FIG. 8 is a bright field micrograph of a microfluidic device 8160 fabricated in poly(dimethylsiloxane) (PDMS) using standard multilayer soft lithography techniques as described in "Soft Lithography", Xia, Y., and Whitesides, G. M., *Angew. Chem. Int. Ed. Engl.*, 1998, 37, 550-575. Briefly SU8 negative epoxy photoresist (MicroChem Corp.) layers were spincoated on a silicon wafer and exposed to UV through mylar photomasks resulting in a patterned master. PDMS was cast against the master and then bonded onto a glass slide.

The operation of the microfluidic device 8160 is essentially identical to that of microfluidic device 4100 illustrated in FIG. 4. As dispersed phase droplets 8101 flow from right to left in the first microfluidic channel 8104 as indicated by flow direction 8110, they pass a series of extraction channels 8102 that are connected to and in communication with the first microfluidic channel 8104 and the second microfluidic channel 8103. Each time each of the dispersed phase droplets 8101 passes a subsequent extraction channel in the series of extraction channels 8102, continuous phase is removed from the first microfluidic channel 8104. After multiple such continuous phase extraction instances, a relatively packed emulsion 8105 results and each droplet flows at approximately the same velocity.

Figure 9:
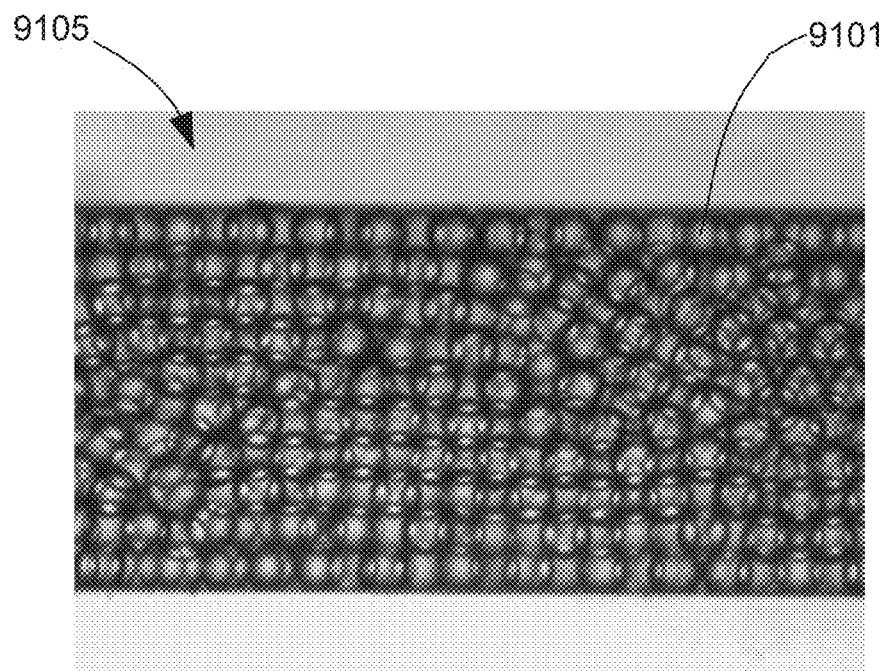
FIG. 9 is a brightfield micrograph illustrating an example of a close-packed emulsion in a microfluidic channel after passing through a system for performing a controlled change in the continuous phase volume fraction of an emulsion in a microfluidic device.

FIG. 9 is a bright field micrograph illustrating an example of a close-packed emulsion in a microfluidic channel after undergoing an extraction process such as in the microfluidic devices discussed previously, according to the present invention. More specifically, FIG. 9 is a bright field micrograph illustrating tightly packed dispersed phase droplets 9101 flowing in a microfluidic channel 9105 after continuous phase extraction.

Methods and Devices for Even Distribution of Droplet in Channels for Parallel Detection In microfluidic reactions, some aspects involve high rates of flow (e.g., 1-1000 drops/second), while other parts of a system may involve slower rates of flow. For example, with optical detection, droplets flow single file past an optical detection point. These droplets may spend less than a microsecond at that point, reducing the number of photons collected over the detection window, thus leading to a small signal to noise ratio. One way to increase signal is to slow the drops down, allowing more photons to be collected over the detection window; however, this also results in slower detection rates. Conversely, other steps in the process may be faster or have an altogether different flow rate and thus different channels may require a different upwards or downwards change in flow rate in order to achieve proper detection.

In some embodiments, a way to evenly distribute droplets in parallel microchannels in order to slow droplets down is provided so that they can be processed by an optical detector rapidly. This process is reversible such that parallel, even flowing channels can be consolidated into a smaller number of faster flowing channels. For example, parallel channels could be used at positions 169-170 of FIG. 1 for multiple parallel detection.

There are two general strategies described here to distribute the droplets evenly in a network of parallel channels. The first is illustrated in FIG. 10, and is to simply fill a very large chamber (10100) with droplets (10103), where the chamber is adjacent to and in fluid communication with, exit channels (10101) whose diameters are on the order of the size of the droplets. Due to the large size (e.g., at least 2×, 3×, 5×, 10×, 20× or more) of the chamber (10100) compared to the exit channels (10101), the pressure drop in the feed channel will be small, so that the drops will be distributed evenly into the exit channels. Once in the exit channels, the drops can either be detected directly, or spaced with the addition of oil before detection. An additional shunt channel (10102), optionally having a larger diameter than the exit channels (10101) can link to each exit channel (10101) and provide a flow of continuous phase fluid The second approach is depicted in FIG. 11 and uses a passive feedback effect to distribute the droplets evenly into a branching network of channels. This is achieved by using a single, narrow channel that branches several times. Shunt channels (11101) (having the same function as the channels 2127 and 3127 in FIGS. 2-3, respectively) at each branch ensure that the droplets flow evenly into the downstream channels. This occurs because when a drop flows into one of the branches, the drop increases the resistance of that branch, so that the other side of the branch has a more direct flow, proving to be more desirable for subsequent drops to flow. Consequently, the next drop will tend to flow into the other side. Provided the resulting behavior of the drops is reasonably periodic between branches, this will result in alternating flow of drops through the branches, and even distribution into the parallel channels. An advantage to this approach over the first approach is that the drops will maintain even flow and spacing into all of the branches, for example in some embodiments, so that an additional spacing step is not necessary.

Using either system specified above or in FIG. 10 or 11 in reverse will allow a larger number of even-flowing input channels to be consolidated into a smaller number of faster moving, even-flowing channels Separating Oil from Drops While Minimizing Drop Dispersion Also provided are methods and devices that are used to separate oil from drops within a microfluidic device, thereby minimizing drop dispersion, i.e., drop mixing. Aspects of this section can be included, for example, in a system as depicted in FIG. 1 at numbers 146-147 or 164-165. Minimizing drop dispersion is useful for improved accuracy in a microfluidic device. The present method removes oil and minimizes dispersion without damaging the drop itself. The present invention provides a method to separate oil from drops and in doing so also decrease the amount of dispersion in drops. The present invention also pertains to a system that minimizes the extent of dispersion of drops during removal of oil from a channel.

In some aspects, rows of posts in line/arranged in parallel with the flow direction are included in a position of a channel, typically in proximity to outlets for oil. The posts within the channel prevent movement of drops except along the direction of flow intended. This constraint reduces the random re-ordering of drops as they enter the channel, allowing them to retain their original time or order association. The use of posts within the channel instead of additional smaller channels minimizes the increased pressure needed to drive fluid through this region. The posts also allow the oil to flow from the middle of the large channel to oil outlets (12103 in FIG. 12) if desired. In some embodiments, the rows of posts include at least 2, 3, 4, 5, 6, 7, 8, 9, 10, or more posts per row. In some embodiments, there are at least 2, 3, 4, 5, 6, 7, 8, 9, or more rows of posts, each substantially parallel. As used herein, a "post" refers to a solid material within a microchannel that may or may not be in contact with both the floor and ceiling of the channel (but is in contact with at least one of the floor or channel) and having a diameter or maximum cross-section that is no more than 0.7, 0.5, 0.3 times the average diameter of droplets in the channel. The posts do not create physical channels per se, but are spaced within a row to substantially prevent movement of droplets between rows. For example, in some embodiments, the distance between posts within a row is no more than 1.5, 1.2, 1.0, 0.9 times the average diameter of droplets in the channel. The distance between rows will be at least the average diameter of a droplet, for example, between 0.9-1.5 times the average droplet diameter.

In some embodiments, outlets are present on two or more sides of the channel, instead of a single outlet or set of outlets, to create a more even outflow.

In some embodiments, the posts are positioned within a gradually widening channel area. For example, the widening can be achieved as a slope angle of 0.1-60 degrees.

Referring to FIG. 12, drops [12100], in a particular order flowing within a narrow channel [12101] gradually flow into a gradually widening channel [12102]. In some embodiments, as the drops [12100] separate from one another within the now wider channel, the oil that the drops are immersed in is removed through suction out of the main area of the channel through small ports [12103], which then flow into parallel sister channels [12104]. The remaining drops [12100] are forced to flow into small rows [12107] that are created by the arrangement of posts [12106] within the channel itself.

Particulate Filters

One function when using droplet-based microfluidics for biological assays can be reinjection of pre-formed drops into a microfluidic device for additional processing. The pre-formed emulsion can be a library, consisting of drops that are nominally the same size, but contain different reagents. For example, as shown in FIG. 1, droplets in 141 and 142 can be pre-formed and then introduced into the channels 144 and 143, respectively. A challenge when re-injecting is introducing the drops in such a way that they do not split or merge, while preventing dust or other contaminants from entering the device.

To prevent dust from entering, filters can be used. In some embodiments, the filters are composed of arrays of structures with narrow gaps capable of trapping particulate. However, normal microfluidic filters can shred re-injected drops into small pieces. Small bits of dust trapped in the filter may also cause multiple drops to merge.

Accordingly, in some embodiments, a filter is provided that will not only create a clean environment within the microfluidic device, but also that will not disturb the drops that are found within the device. In some embodiments, a device referred to herein as a "droplet filter," which filters dust from a pre-formed emulsion while allowing drops to pass without breaking apart or passing through drops that have coalesced on dust particles, is provided. In some embodiments, the droplet filter has a geometry that can effectively filter an emulsion, preserving the contents of the droplets in the emulsion while substantially filtering dust or particulate. Furthermore, in some embodiments, this geometry does not have high aspect ratio features (thickness: width), typically under 1:1, such that it can be injection molded for thermoplastic microfluidic devices.

In some embodiments, the droplet filter is composed of an array of posts, however, further comprise one or more of the characteristics, as described in the paragraphs below.

In some embodiments, a layer step is added in the flow path, prior to the post array, which acts as a holding point for most hydrophobic particulate. This layer represents a difference in thickness, such that drops are constrained and must compress to flow through.

In some embodiments, when pores are sized to achieve the proper degree of filtration, the hydrodynamic resistance across the filters can be very high. One option to reduce the resistance is to make the pores very tall and narrow in width. Unfortunately, this can allow particulate to pass and create geometries that are hard to fabricate. Accordingly, in some embodiments, the hydrodynamic resistance is reduced by placing pores on a different layer thickness, such that the region of high resistance is minimized, and the features are not high aspect ratio (1:1/thickness:width). This results in proper filtration and as well as a filter that can be fabricated by conventional methods of thermoplastic injection molding.

The posts of the filter, which are within the reduced thickness region, can be spaced such that the drops tend to flow through without breaking into smaller drops. Droplet interfaces are under strain by shear stresses in different directions, imposed by space constraints. The pore width, the constraining layer thickness, and even the effect of other drops, can all affect droplet break off and coalescence. The existing layout ensures that the shear stresses are minimized for the required degree of filtration.

In some embodiments, the spacing between successive rows of the filters is much larger than the drops, allowing the drops to pass through and not be stressed by multiple constraining pores at one time. In some embodiments, the filter posts that form the array are much larger than the drops, or the flattened projection of the drops, within the filter region. This ensures drops are not deformed across a post, and improves the stability of the filter. It also establishes a holding pattern, such that drops are directed between the pores, as opposed to in tension across a post.

By staggering or placing adjacent posts or filter pores in line with each other, filtration can be achieved in a way that prevents particulate from either causing droplet breakup or coalescence, which can result in hydrodynamic resistance and potentially droplet-destructive regions. In some embodiments, the droplet filter comprises three rows of circular posts, such that the post array is in a, e.g., 9 µm, thickness region, and the surrounding areas are in, e.g., 20 µm thickness. The droplets are therefore compressed as they enter the 9 µm region.

The drops are then further compressed by flowing through (e.g., 9 µm) pores, in moving between posts within the region. Successive rows aid in capturing non-rigid particulates that makes it through prior rows. The alignment of posts is depicted as linear in FIG. 13, but can be angled or oriented in any way that reduces resistance or better aids in capturing particulate.

The following describe the features described within FIGS. 13, 14A, 14B, and 14C: Inlet port (13101), Flow direction (13102, 14102), Filter post (13103, 14103A, 14103B), Outlet port (13104), Drop before filter (14110), Drop within filter (14111), Drop after filter (14112), Channel height change (14113)

High Speed Spacing

Droplet-based microfluidic devices perform biological assays within droplets by performing a series of functions on the drops. For example, to perform sequencing reactions, droplets can be loaded with target DNA, and then merged with droplets containing probes or primers, enzymes, and other sequencing reagents. In such reactions, it is extremely helpful to be able to accurately manipulate individual droplets.

One way to ensure one-to-one interactions is to space the droplets by adding continuous phase to the emulsion. This is achieved, for example, by flowing the drops single file down a narrow channel (e.g., approximately the width of the droplets), and then using a second channel to add additional continuous phase. As the flow rates are increased, however, to flow the droplets faster or to add greater amounts of continuous phase, viscous forces applied to the drops can become significant, causing the droplets to break into smaller drops. Accordingly, the methods and devices described herein provide a microfluidic droplet spacer that can space droplets controllably and at very fast rates without causing them to break into smaller drops.

One use of the droplet spacer is to controllably space the drops without breaking them. In some embodiments, the droplets are spaced so that they are regularly periodic as the droplets exit the spacer, do not coalesce as the droplets pass through the spacer, and do not break apart. To ensure periodic spacing, the drops can be packed closely as they enter the spacer, and the spacer inlet can be narrow enough such that the drops can enter only single file, i.e., the inlet, for example, is less than two average droplet diameters wide, and in some embodiments is less than 1.9, 1.8, 1.7, 1.6, 1.5, 1.4, 1.3, 1.2, or 1.1× the average droplet diameter. However, to prevent the drops from breaking, the channel can be initially wide and then narrow gradually, so that the viscous forces applied to the drops are small as the continuous phase is added.

One challenge, though, is that since the channel is initially narrow to make the drops single file, expanding the channel abruptly so that the continuous phase can be added gently can apply large extensional forces to the drops that can cause them to break or even coalesce. Thus, in the presently described spacer, a gentle graduation 15007 (e.g., at a slope of 0.01-60 degrees) is used, which applies minimal extensional shear to the drops before the continuous phase is added. The narrowing is also achieved gently 15008 (e.g., at a slope of 0.1-60 degrees), so that minimal longitudinal shear is applied to the drops during the spacing. The gentle effect can be achieved, for example, by the inclusion of curved corners 15009, rather than corners forming right angles, and construction of the junction such that the width of the droplet channel gradually widens at the junction and then narrows back to the original channel width gradually past the junction.

In some embodiments, the droplet spacer is composed of a T-junction geometry in which the droplets are introduced from one channel and the spacing fluid from an inlet. See, e.g., FIG. 15. Where the inlet intersects the channel, the channel widens gradually; allowing the drops to enter single file and to be spaced by addition of oil, while reducing the viscous forces applied to the drops. This allows the drops to be spaced and moved into a device without breaking into smaller drops, even at flow rates that typically result in large amounts of breakage. The slope of the expanding and constricting walls at the spacer should be selected to apply the minimal shear to the drops, while still allowing effective spacing. In another possible embodiment, curved walls can be used, to modulate the force as the drops pass.

Systems and Methods for Spacing Sets of Droplets in a channel

In some embodiments, systems and methods for spacing sets of drops within a microfluidic channel are provided. More specifically, the present system provides for three alternate methods of spacing sets of drops within a channel as to provide for more precise data collection and analysis. In one embodiment of the invention, a microfluidic system is used is set forth in FIG. 1 or as described in PCT/US2013/5917.

A first possible method describes a "spacer" drop (a large drop relative to the size of channel itself and in comparison to the drops within the channel containing sample material to be analyzed) being injected into the channel at a precise moment in time, determined by a monitor system that detects when drop sets are transitioning (FIG. 17). Here, the "spacer" drop can be comprised of a fluid that is immiscible in the carrier fluid of the emulsion; thus, the spacer drop is not meant to be used for analysis or any sort of reaction within the system, but merely divides sets of other drops.

The second possible embodiment describes a method similar to the above mentioned method, except this embodiment does not require use of a monitor system for precise timing of the injection of spacer drop. Here, the immiscible carrier fluid which creates the spacer drops is introduced into the channel at a regular, continuous flow rate. This flow rate is set so as to produce the subsequent spacer drops at a frequency that enables the number of drops spaced to be about the same as, or less than, the minimum number of drops originally injected or requiring separation (drop sets). In this situation, the collection of drops between spacers is at most from two distinct populations (FIG. 18). This method results in a binary method of separating any two pairs of populations from each other, which is far more desirable in data collection than no spacing of drops at all.

Another possible embodiment describes a method similar to the above mentioned method, except in this embodiment the packed drops are exposed to an electrical field which transitions between "on" and "off" by a predetermined interval (FIG. 19). When the field is set to "on," drops merge together, creating a larger "spacer" drop within the channel, removing the need for an additional injection site as in the above two embodiments and thereby creating sets of two possible sets of drops within the channel, making detection and analysis significantly easier.

In some embodiments, a system and method are provided for spacing sets of drops within a microfluidic channel. More specifically, in some embodiments, the present system provides for alternate methods of spacing sets of drops within a channel so as to provide for more precise data collection and analysis. In one embodiment, a sample is present within a vehicle (e.g., a droplet in an emulsion) in a microfluidic device. In one aspect of this embodiment, multiple samples (i.e., more than one) may be present together in the same vehicle and/or may be separated into individual samples within individual vehicles at any point during an assay(s). As an example, FIG. 1 depicts a system where two differentially-labeled drops alternate (coming from 141 and 142), include a sample that is amplified and forming amplified droplets 156 that alternate in labeling. Portions of the inflated droplets 156 are injects into probe droplets 160 such that portions from a first droplet 156 merged into droplets 160 form a first set and droplets from a second inflated droplet 156 into probe droplets 160 form a second set, etc., such that sets are defined as comprising portions from the same inflated droplet 156. Additionally, a vehicle (e.g., droplet) comprising one or more samples may become larger or smaller (e.g., by way of inflation or partitioning, respectively) in size, volume or content during the performance of an assay. A vehicle may be amplified and/or subdivided one or more times during the performance of an assay. The system may further perform a "cascading assay," which is a series of multiple (i.e., more than one) assays, wherein each assay may be the same or different, and wherein each assay in the series may further comprise one or more process or step. In one aspect of this embodiment, the sample is present on a carrier within a vehicle in a microfluidic device.

FIG. 16 illustrates one embodiment of a microfluidic channel comprising two picoinjectors injecting two different samples 16163 and 16156 into a probe drop 16160. As drop 16160 passes the first injection site 16162, the drop 16160 is injected with sample 16163, resulting in drop 16180. Drop 16180 then continues down the channel until it reaches injection site 16161, where 16180 is then injected with sample from a slug (here, depicted by the number "5"), resulting in drop 16173. Drop 16173 then continues down the channel until the channel widens for incubation purposes, as is depicted by 16183. The illustration shows that without any additional mechanism added to the channel 16170, the drops downstream of the injection sites 16162 and 16161 lose injection orientation, resulting in a mixing of drops 16183, 16184, and 16185 (i.e. the mixing of drops 5, 4, 3, 2, as illustrated in the figure).

Additionally, FIG. 16 illustrates that as one particular slug containing a different sample (numbers "5," "6," and "7," respectively) are partitioned into the flowing drops sequentially so as one particular material is used up in the passing drops, the next slug containing a different sample begins to enter the drops, resulting in "sets" of drops containing partitions of different but sequential samples within the channel (16183, 16184 and 16185).

FIG. 17 illustrates one possible embodiment of the invention. A microfluidic channel comprising two picoinjectors injecting two different samples 18163 and 18156 into a probe drop 18160. As drop 18160 passes the first injection site 18162, the drop 18160 is injected with sample 18163, resulting in drop 18180. Drop 18180 then continues down the channel until it reaches injection site 18161, where 18180 is then injected with material from a slug (here, depicted by the number "5"), resulting in drop 18173. Drop 18173 then continues down the channel until the channel widens for incubation purposes, as is depicted by 18183. By way of example, an electric field from electrodes 18181 and 18182 facilities the material transfer, though other mechanisms of disrupting the droplet interface to accomplish injection are also possible, such as those methods described above. Drop 18180 continues down channel 18170 until it reaches a second injection site, 18161. Here, alternating slugs 18186 (5, 6, and 7 are illustrative of slugs with different material components) are similarly incorporated into drop 18180 via similar means as described above 18182. This results in drop 18173, which now contains material from both 18163 and 18186. As drop 18173 continues down the channel, a port 18187 is incorporated into the channel just before the channel widens for incubation 18185. The port 18187, generates a large drop 18188 of an immiscible fluid into the channel, separating drops 18173 which contain different material from injection port 18186 (samples 5, 6, and 7, respectively). The timing of the injection is based on a closed loop observation of the transition between slugs 18186. The observation mechanism 18190 can be a discrete optical system such as a photo detector, i.e. PMT, photodiode, or phototransitor; an imaging system such as a CCD or CMOS camera; capacitive; pressure; or electric field. This results in a large drop 18189 (relative to the diameter of the channel and corresponding material-filled drops) separating groups drops containing similar material 18184 and 18183 when sets contain a maximum known number of species such as one, two, three, four, five, etc., effectively inhibiting the mixing of drops within the channel.

FIG. 18 illustrates another possible embodiment of the invention: A microfluidic channel comprising two picoinjectors injecting two different samples 19163 and 19156 into a probe drop 19160. As drop 19160 passes the first injection site 19162, the drop 19160 is injected with sample 19163, resulting in drop 19180. Drop 19180 then continues down the channel until it reaches injection site 19161, where 19180 is then injected with material from a slug (here, depicted by the number "5"), resulting in drop 19173. Drop 19173 then continues down the channel until the channel widens for incubation purposes, as is depicted by 19183. As the drop 19173 continues down the channel, a port 19187 is incorporated into the channel at advantageous locations for incubation 19185. An immiscible fluid in 19187 flows continuously in to the channel at a fixed rate or pressure expanding into the channel 19188 and breaking off to make spacer drops 19188 in a natural periodic fashion. The spacer drops 19188 separate those drops containing material 19183 and 19184. For example, here the group of drops 19184 is composed of drops containing material 3 and 4, and the group of drops 19183 is comprised of drops containing samples 4 and 5. Groups may compose drops containing material two, three, four, five, etc.

FIG. 19 illustrates another possible embodiment of the invention: A microfluidic channel comprising two picoinjectors injecting two different samples 20163 and 20156 into a probe drop 20160. As drop 20160 passes the first injection site 20162, the drop 20160 is injected with sample 20163, resulting in drop 20180. Drop 20180 then continues down the channel until it reaches injection site 20161, where 20180 is then injected with material from a slug (here, depicted by the number "5"), resulting in drop 20173. Drop 20173 then continues down the channel until the channel widens for incubation purposes, as is depicted by 183. Here, alternating slugs 20186 (5, 6, and 7 are illustrative of slugs containing different material) are incorporated into drop 20180 by disrupting the interface of the drop via electrical field or any other means of disruption 20182. This results in drop 20173, which now contains material from both 20163 and slug 20186. As the drop 20173 continues down the channel, a second electric field from electrodes 20190 and 20191 is introduced to the channel, which turns on and off in a periodic fashion illustrated in 20193. When the electric field at 20190 and 20191 is turned on, the drops that are in the field's proximity will merge, creating a large drop containing the contents of multiple different drops 20192 (here, for example, drops containing material 4 and 5 are now merged). The field is kept on for enough time to merge enough drops to generate a large enough spacer drop 20189 that will fully separate groups of drop species. Within the widened part of the channel 20185, the combined drop 20192 is illustrated as drop 20189 downstream and effectively separates groups of drops as in FIG. 18; therefore, group 183 is a combination of drop species by way of example with samples 4 and 5, and group 184 contains a combination of drops with samples 3 and 4. Groups may compose drops containing material two, three, four, five, etc.

EXAMPLES

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

In one example, the present invention may be used to as part of a system (e.g., as depicted in FIG. 1) to perform methods for detecting the presence or absence of a particular nucleic acid sequence in a sample. A nucleic acid sample (148) may be injected into the system by the user. The system then injects this sample into a multitude of droplets (150), present within an emulsion, containing the reagents necessary for a polymerase chain reaction (PCR) amplification reaction. These droplets contain the appropriate oligonucleotide primers, with the droplets being referred to as "PCR droplets." The PCR droplets may have a label which allows them to be distinguished between neighboring PCR droplets. In other words, an alternating label, to ensure that signal originating from a single PCR droplet not be assigned to multiple droplets and that signal originating from multiple droplets not be assigned to a single droplet. Next, the PCR droplets are thermally cycled for PCR amplification. PCR, using water-in-oil emulsions may be done using standard PCR conditions, as will be known and understood by one of skill in the art and described, for example, by Williams, et al., "Amplification of Complex Gene Libraries by Emulsion PCR", Nature Methods (2006), vol. 7, pp. 545-50; Diehl, et al., "BEAMing: Single-Molecule PCR on Microparticles in Waterin-Oil Emulsions", Nature Methods (2006), vol. 7, pp. 551-59; and Porreca, et al., "Polony DNA Sequencing", In: F. Ausubel, ed. 2006. Curr Protoc Mol Biol., Chapter 7, Unit 7.8. After PCR, each of the PCR droplets (156) is injected into a multitude of probe droplets (160). For example, the probe droplets may contain nucleic acid probes and the chemical reagents necessary for a probe hybridization assay. In this example, the assay may result in fluorescent signal only if the probes hybridize to the injected nucleic acid sample, as described in WO 2012/078710. The data acquired is processed and analyzed by the system of the present invention. Accordingly, data from multiple probe droplets may be used for DNA sequencing of a nucleic acid sample, as described in WO 2012/078710, if data from multiple probe drops can be assigned as originating from a single PCR drop.

Data from multiple probe droplets can be assigned as originating from a single PCR droplet, if adjacent PCR droplets have distinguishable labels and if the order of droplets flowing in the network is maintained.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A system for labeling and alternating flow of differentially-labeled droplets, the system comprising:
   at least one inlet for droplets within a continuous phase,
   at least two microfluidic channels that are connected to the at least one inlet at one end and form a junction with a joint microfluidic channel at the other end,
   a connection channel configured to allow the continuous phase fluid but not the droplets to flow between the microfluidic channels, wherein the connection channel is sized such that the droplets are too large to enter one of the microfluidic channels, and wherein the connection channel is configured to equalize pressure between the two microfluidic channels, and
   a labeling device configured to label droplets in one of the microfluidic channels;
   wherein when the droplets flow through the at least two microfluidic channels toward the joint microfluidic channel, the labeling device labels the droplets that flow in one of the microfluidic channels.

2. The system of claim 1, wherein said label is an immiscible label.

3. The system of claim 1, wherein the labeling device labels the droplets through disrupting the interface between the immiscible label and the continuous phase.

4. The system of claim 3, wherein the labeling device uses an electric field to disrupt the interface between the immiscible label and the continuous phase.

5. The system of claim 3, wherein the labeling device comprises one or more electrodes that generate an electric field to disrupt the interface between the immiscible label and the continuous phase.

6. The system of claim 3, wherein the droplets in the microfluidic channel is spaced so that neighboring droplets do not coalesce due to the presence of the electric field.

7. A method for labeling droplets and alternating flow of differentially-labeled droplets in the system of claim 1, the method comprising the steps of:
   injecting a plurality of droplets within a continuous phase into the at least one inlet, and
   labeling the droplets in one of the microfluidic channels with a label using the labeling device, wherein labeled and unlabeled droplets enter the joint microfluidic channel in a substantially alternating fashion.

8. The method of claim 7, wherein said label is an immiscible label.

9. The method of claim 7, wherein the droplets contain primers and reagents that are necessary for a desired PCR reaction.

10. The method of claim 7, wherein the labeling device labels the droplets through disrupting the interface between the immiscible label and the continuous phase.

11. The method of claim 10, wherein the labeling device comprises one or more electrodes that generate an electric field to disrupt the interface between the immiscible label and the continuous phase.

12. The method of claim 11, wherein the droplets in the microfluidic channel is spaced so that neighboring droplets do not coalesce due to the presence of the electric field.

* * * * *